(12) United States Patent
Hayashi

(10) Patent No.: US 10,574,968 B2
(45) Date of Patent: Feb. 25, 2020

(54) STEREOSCOPIC PICTURE GENERATION APPARATUS AND STEREOSCOPIC PICTURE GENERATION METHOD

(71) Applicant: SONY CORPORATION, Tokyo (JP)

(72) Inventor: Tsuneo Hayashi, Chiba (JP)

(73) Assignee: SONY CORPORATION, Tokyo (JP)

(*) Notice: Subject to any disclaimer, the term of this patent is extended or adjusted under 35 U.S.C. 154(b) by 177 days.

(21) Appl. No.: 14/893,423

(22) PCT Filed: Aug. 14, 2014

(86) PCT No.: PCT/JP2014/004193
§ 371 (c)(1),
(2) Date: Nov. 23, 2015

(87) PCT Pub. No.: WO2015/037185
PCT Pub. Date: Mar. 19, 2015

(65) Prior Publication Data
US 2016/0105659 A1  Apr. 14, 2016

(30) Foreign Application Priority Data

Sep. 11, 2013  (JP) .................. 2013-188377

(51) Int. Cl.
*H04N 13/211* (2018.01)
*H04N 13/282* (2018.01)
(Continued)

(52) U.S. Cl.
CPC ....... *H04N 13/211* (2018.05); *A61B 1/00193* (2013.01); *G02B 21/0012* (2013.01); *G02B 21/22* (2013.01); *H04N 5/2251* (2013.01); *H04N 13/282* (2018.05); *A61B 1/063* (2013.01); *A61B 1/0638* (2013.01); *G02B 23/2415* (2013.01); *H04N 2005/2255* (2013.01)

(58) Field of Classification Search
CPC ... A61B 1/00193; A61B 1/063; A61B 1/0638; G02B 23/2415; G02B 21/22; G02B 21/0012; H04N 13/021; H04N 13/0282; H04N 5/2251; H04N 2005/2255
USPC ......................................................... 348/47
See application file for complete search history.

(56) References Cited

U.S. PATENT DOCUMENTS 5,588,948 A   12/1996  Takahashi et al.
5,720,706 A   2/1998   Takahashi et al.
(Continued)

FOREIGN PATENT DOCUMENTS

CN   102388619 A    3/2012
JP   2002-344999 A  11/2002
(Continued)

OTHER PUBLICATIONS

English Translation of Japanese Publication 2006-050320 Feb. 2006.*

(Continued)

*Primary Examiner* — Loi H Tran
(74) *Attorney, Agent, or Firm* — Xsensus LLP

(57) ABSTRACT

An information processing apparatus includes an image pickup element which acquires at least three images of an object, each image corresponding to a different perspective of the object; and a control unit which selectively combines subsets of the images to generate stereoscopic images.

20 Claims, 25 Drawing Sheets

(51) Int. Cl.
*A61B 1/00* (2006.01)
*G02B 21/00* (2006.01)
*G02B 21/22* (2006.01)
*H04N 5/225* (2006.01)
*G02B 23/24* (2006.01)
*A61B 1/06* (2006.01)

(56) References Cited

U.S. PATENT DOCUMENTS

| | | | |
|---|---|---|---|
| 2012/0019736 A1* | 1/2012 | Yamamoto | G03B 35/02 349/15 |
| 2012/0056997 A1* | 3/2012 | Jang | H04N 13/218 348/47 |
| 2013/0016188 A1 | 1/2013 | Ogasahara | |
| 2015/0015672 A1* | 1/2015 | Iwasaki | H04N 5/23229 348/46 |

FOREIGN PATENT DOCUMENTS

| | | |
|---|---|---|
| JP | 2006-50320 A | 2/2006 |
| JP | 2010-268443 A | 11/2010 |
| JP | 2012-15820 A | 1/2012 |
| WO | WO 2012/043003 A1 | 4/2012 |
| WO | WO 2012/043211 A1 | 4/2012 |
| WO | WO 2012/137485 A1 | 10/2012 |

OTHER PUBLICATIONS

Japanese Office Action dated Mar. 14, 2017 in Patent Application No. 2013-188377 (with English Translation).
Combined Chinese Office Action and Search Report dated Jan. 17, 2017, in Patent Application No. 201480046593.3 (with English translation).
International Search Report dated Oct. 23, 2014 in PCT/JP2014/004193.
European Office Action dated Jul. 12, 2017 in Patent Application No. 14 762 101.5.
Combined Chinese Office Action and Search Report dated Sep. 22, 2017 in Patent Application No. 2014800465933 (with English language translation).

* cited by examiner

[Fig. 1]
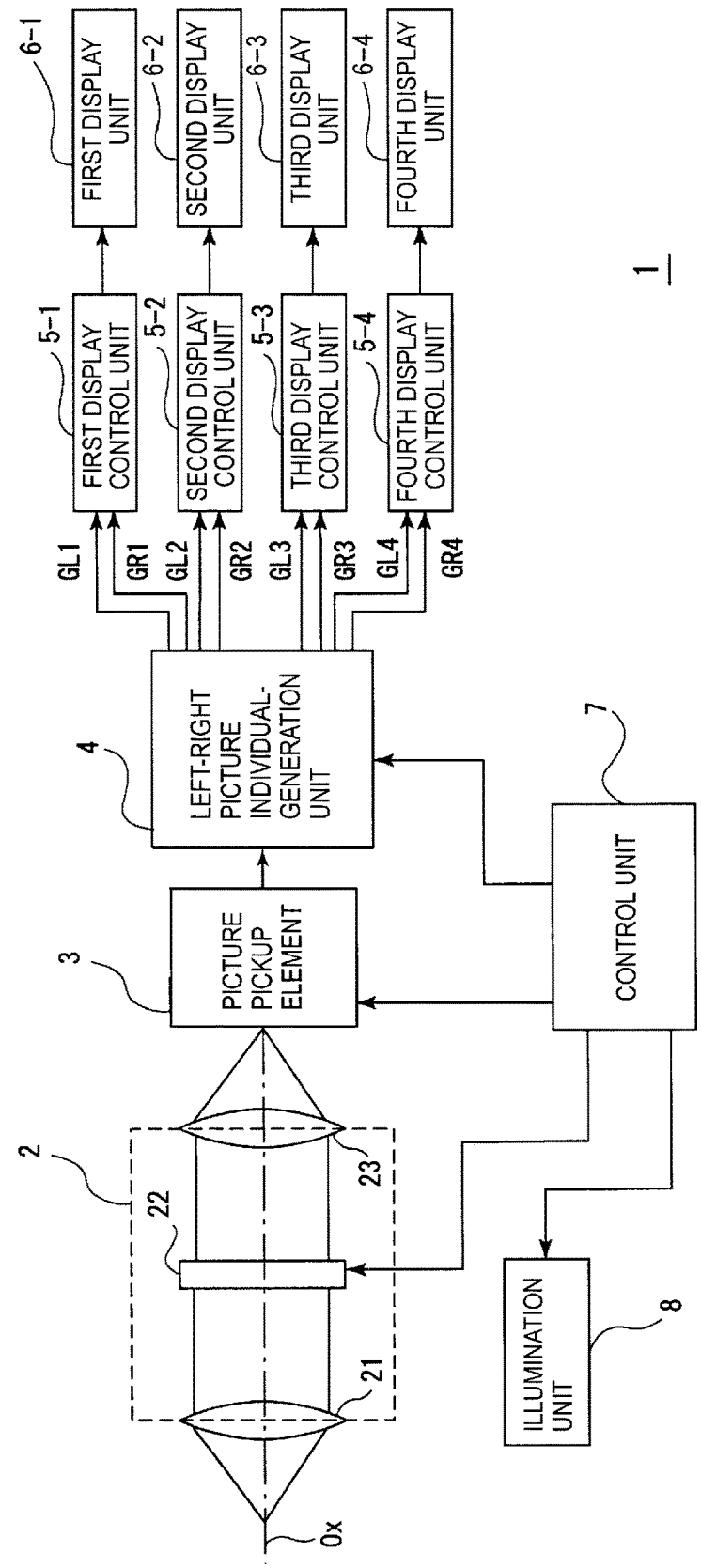

[Fig. 2]
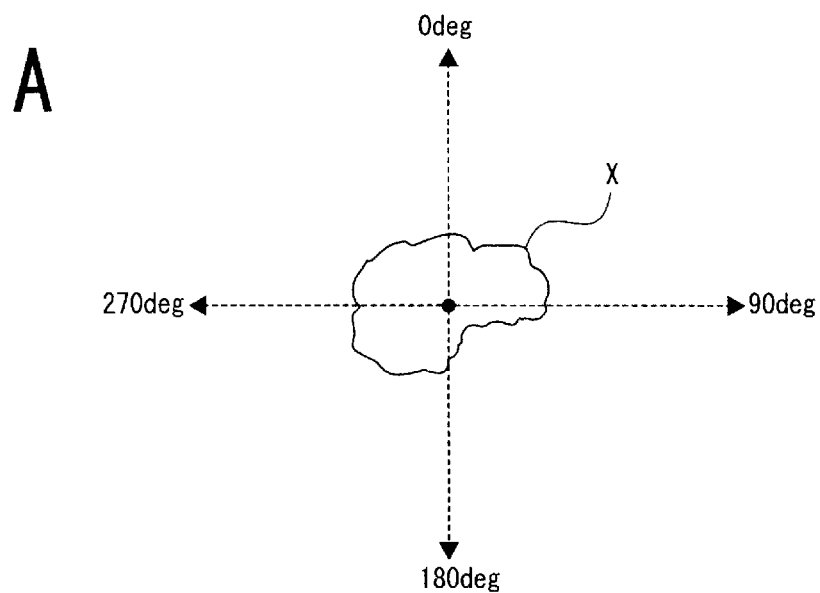
A
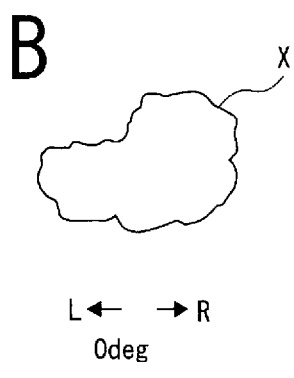
B
L ← → R
0deg
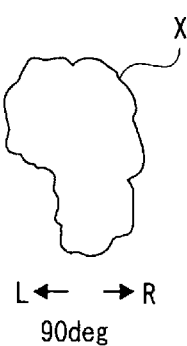
C
L ← → R
90deg
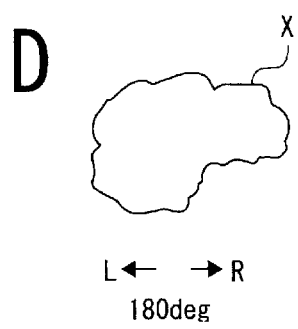
D
L ← → R
180deg
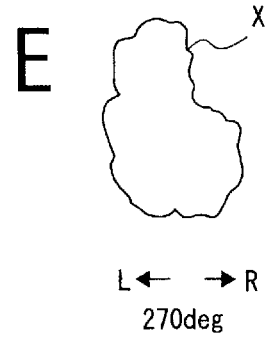
E
L ← → R
270deg

[Fig. 3]
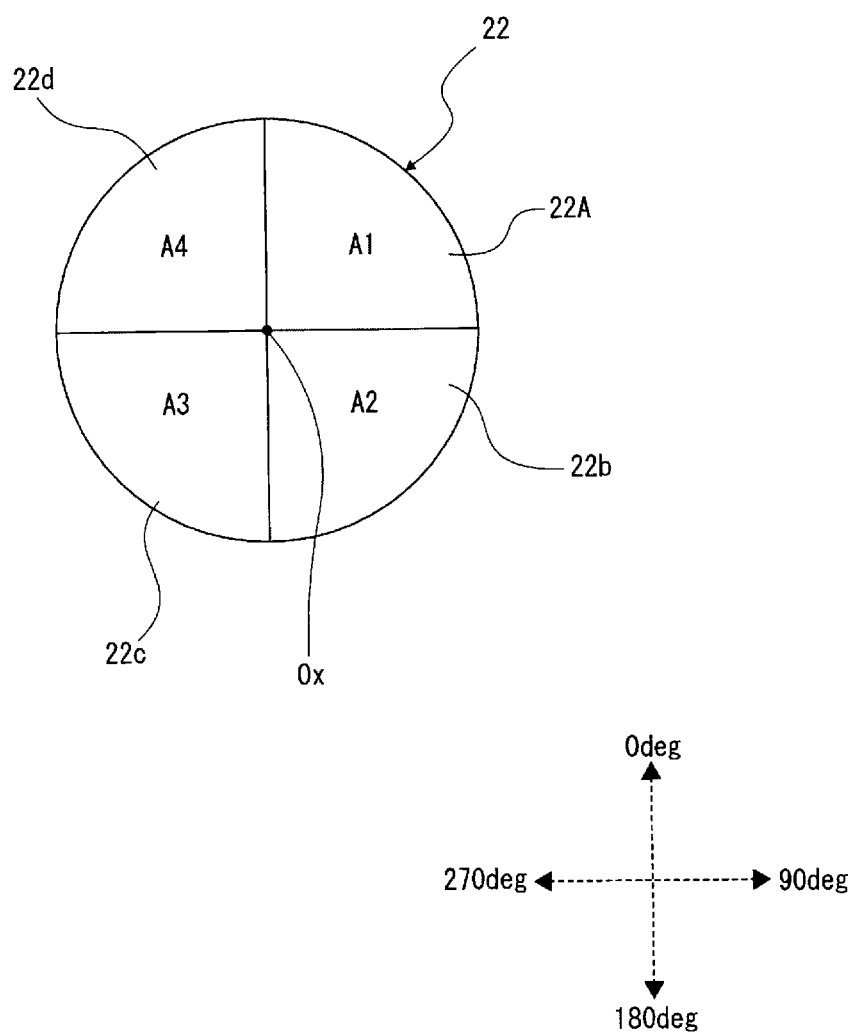

[Fig. 4]
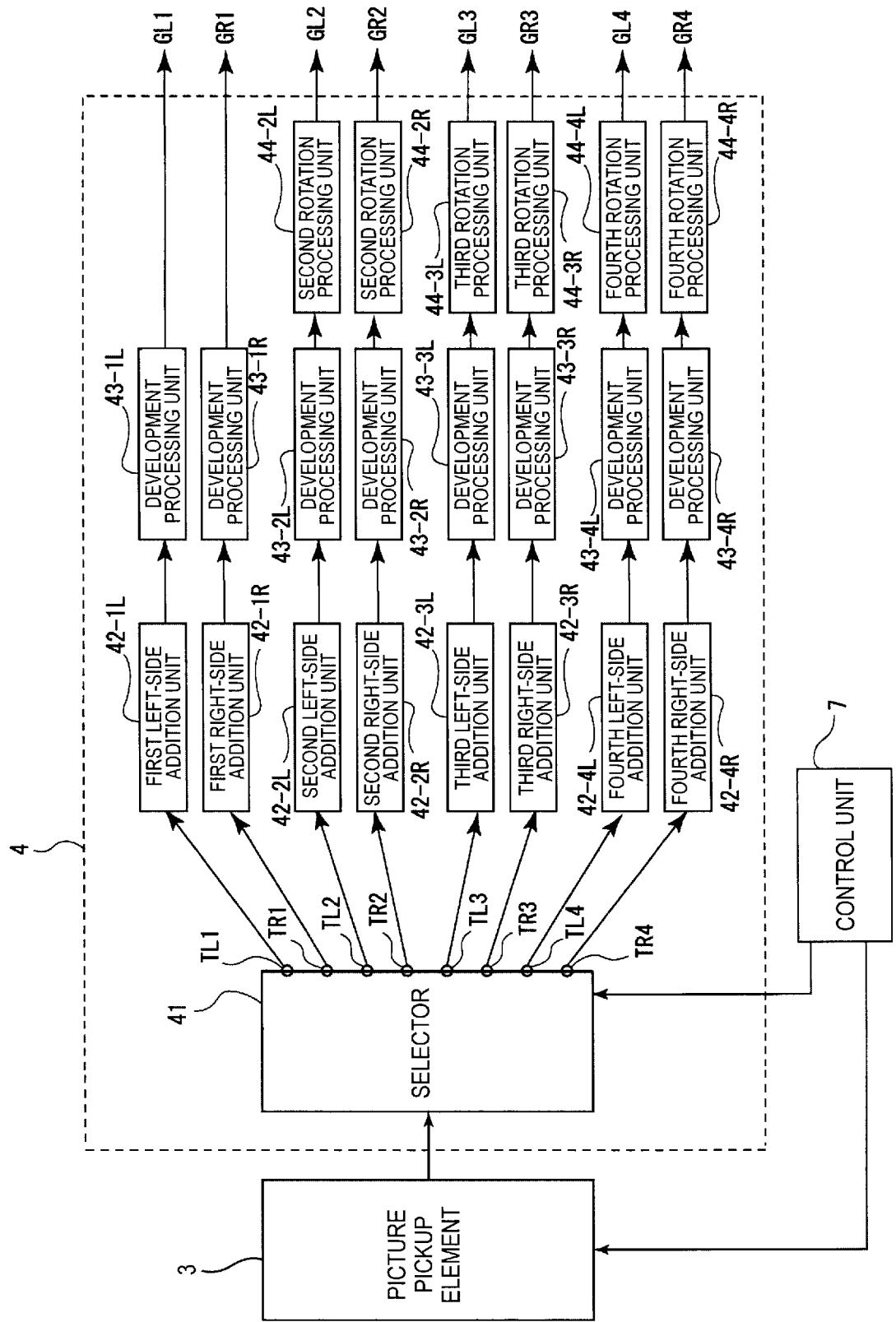

[Fig. 5]
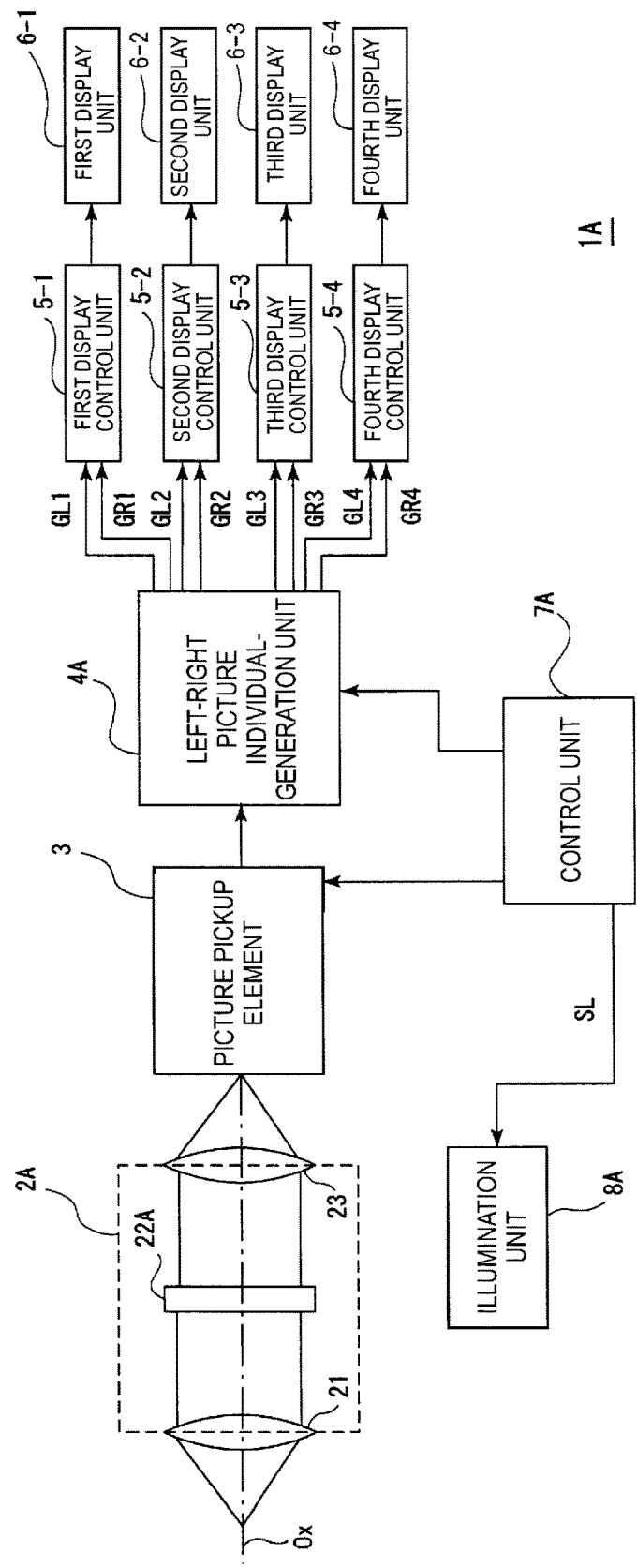

[Fig. 6]
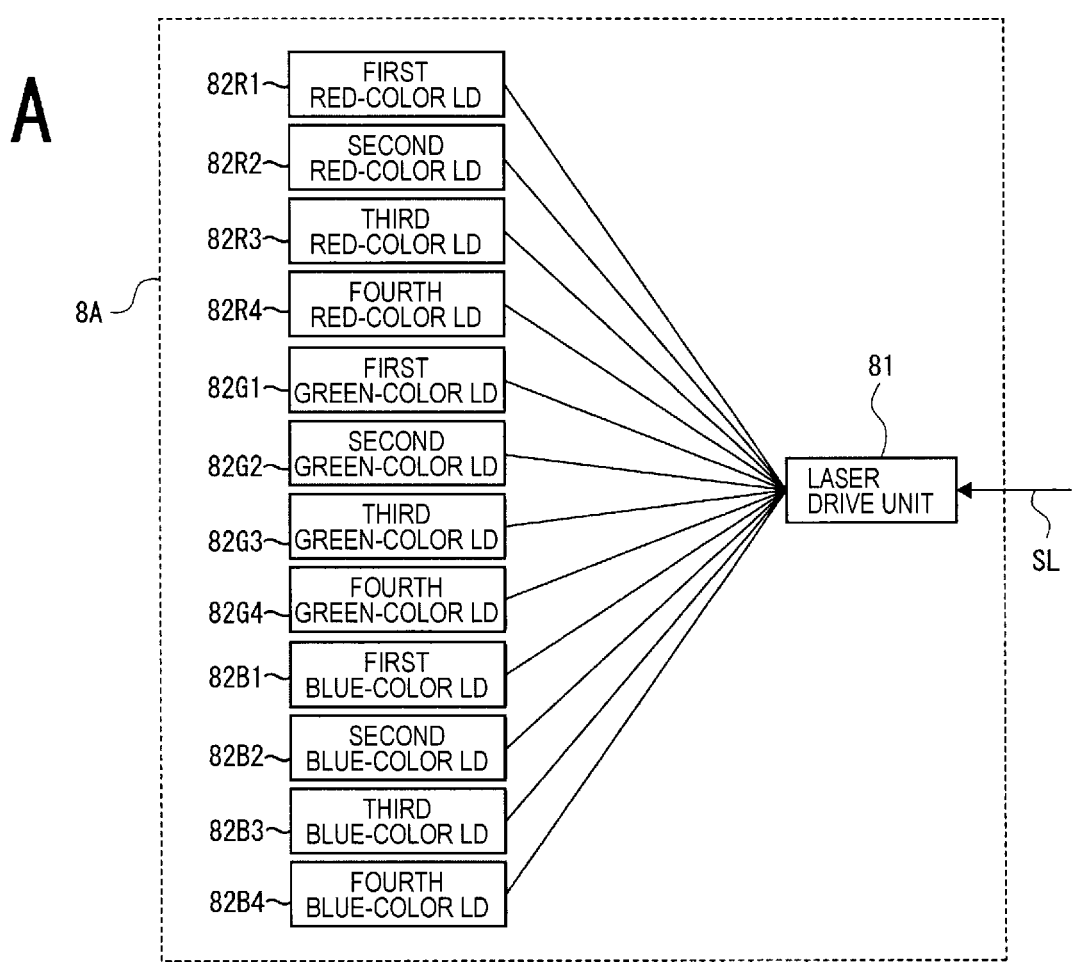
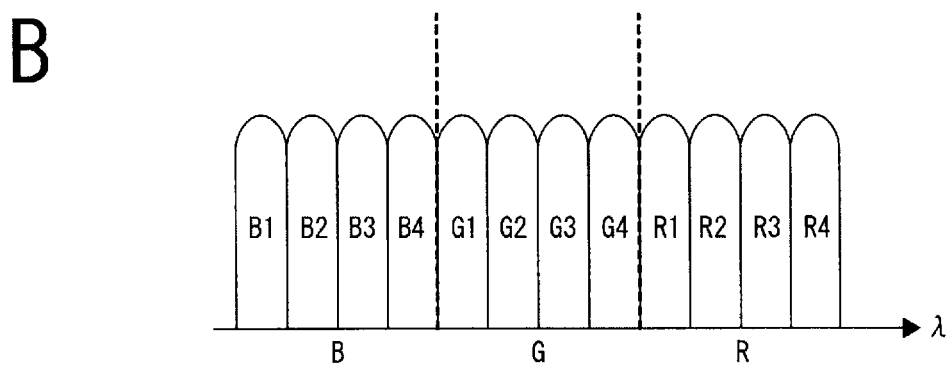

[Fig. 7]
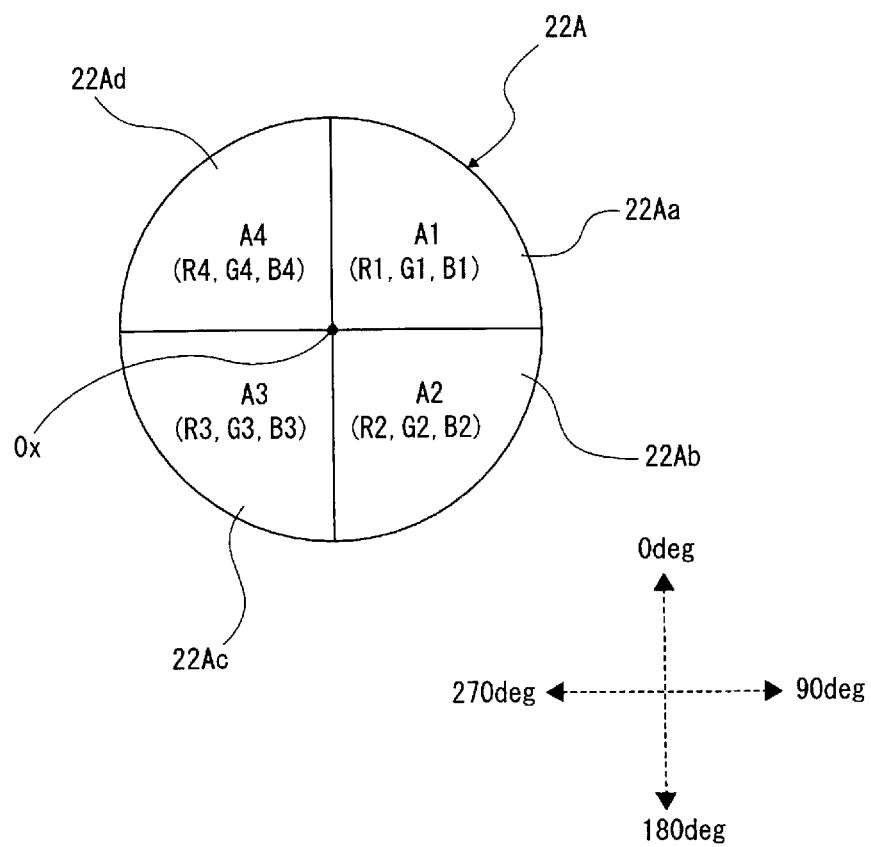

[Fig. 8]
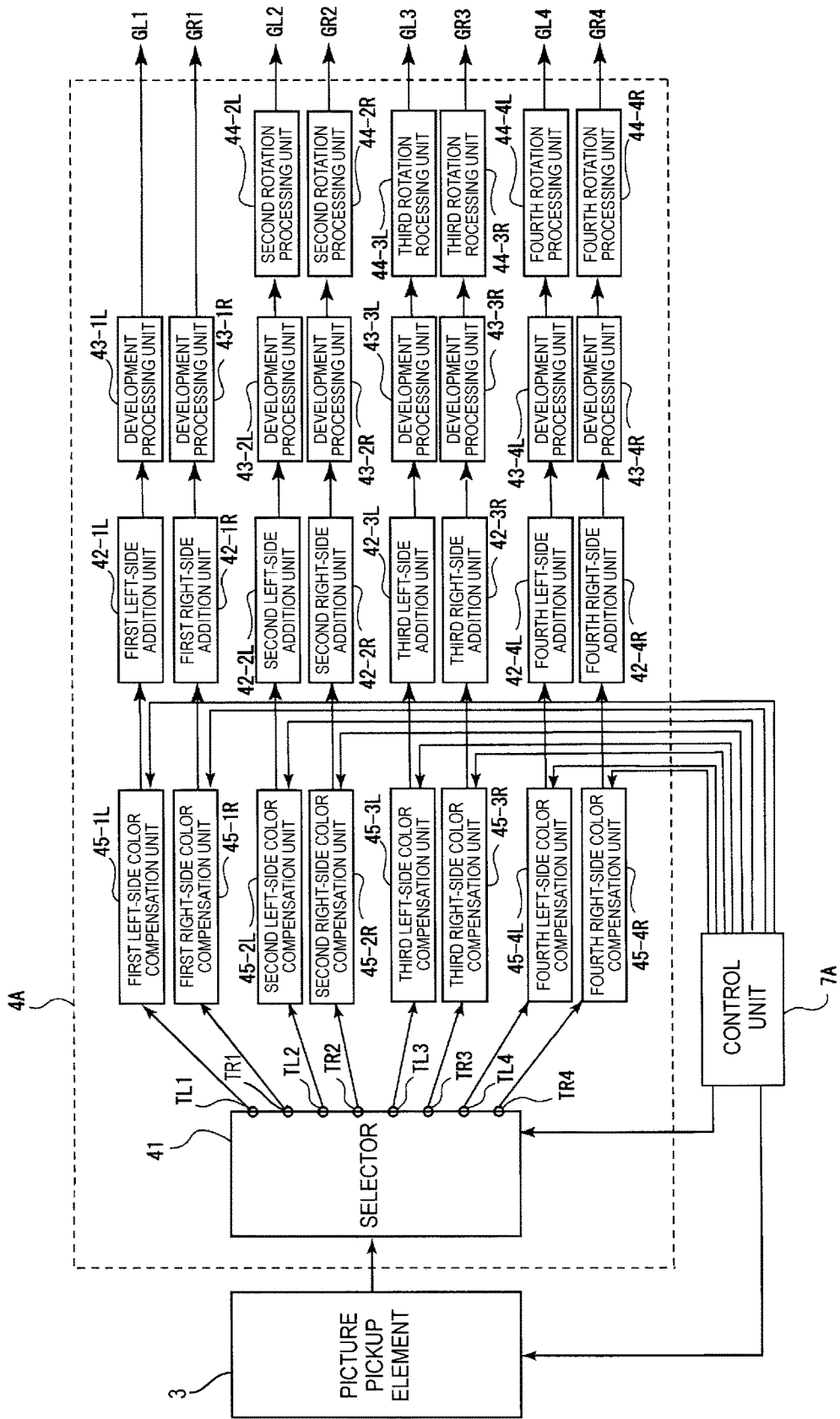

[Fig. 9]
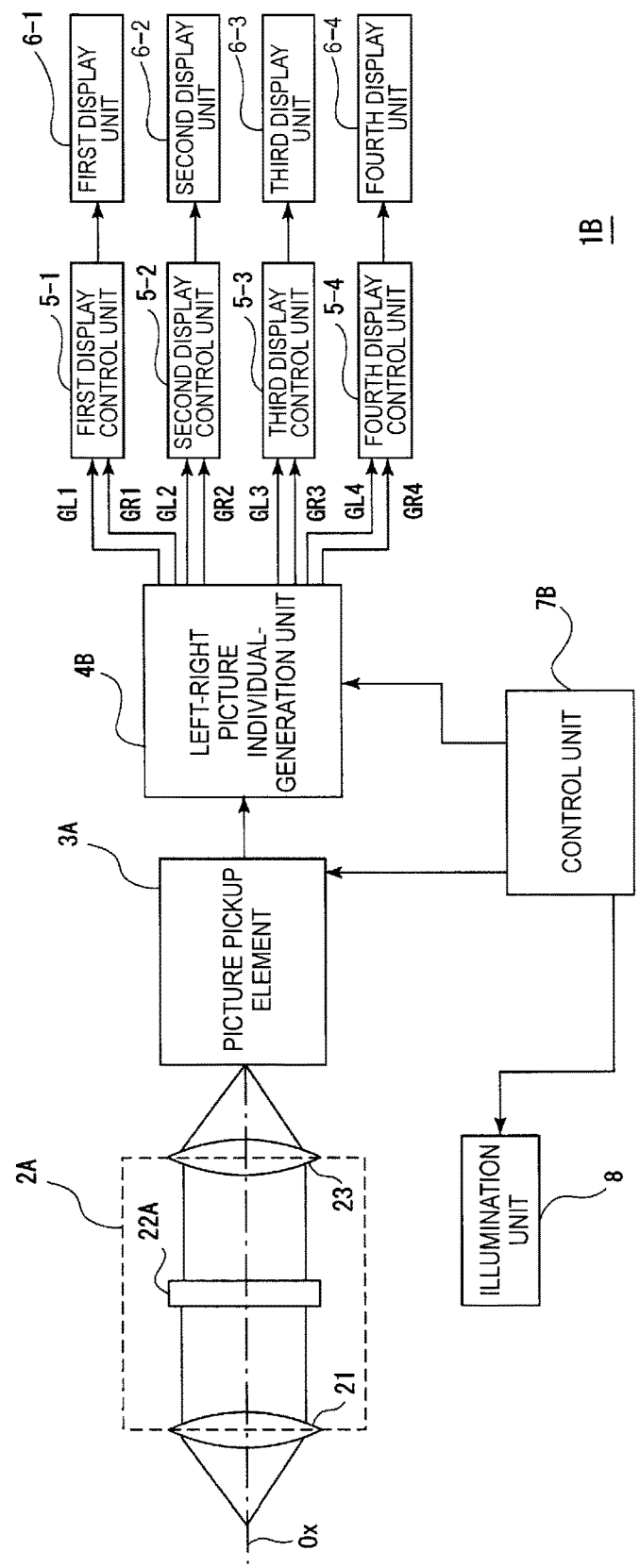

[Fig. 10]
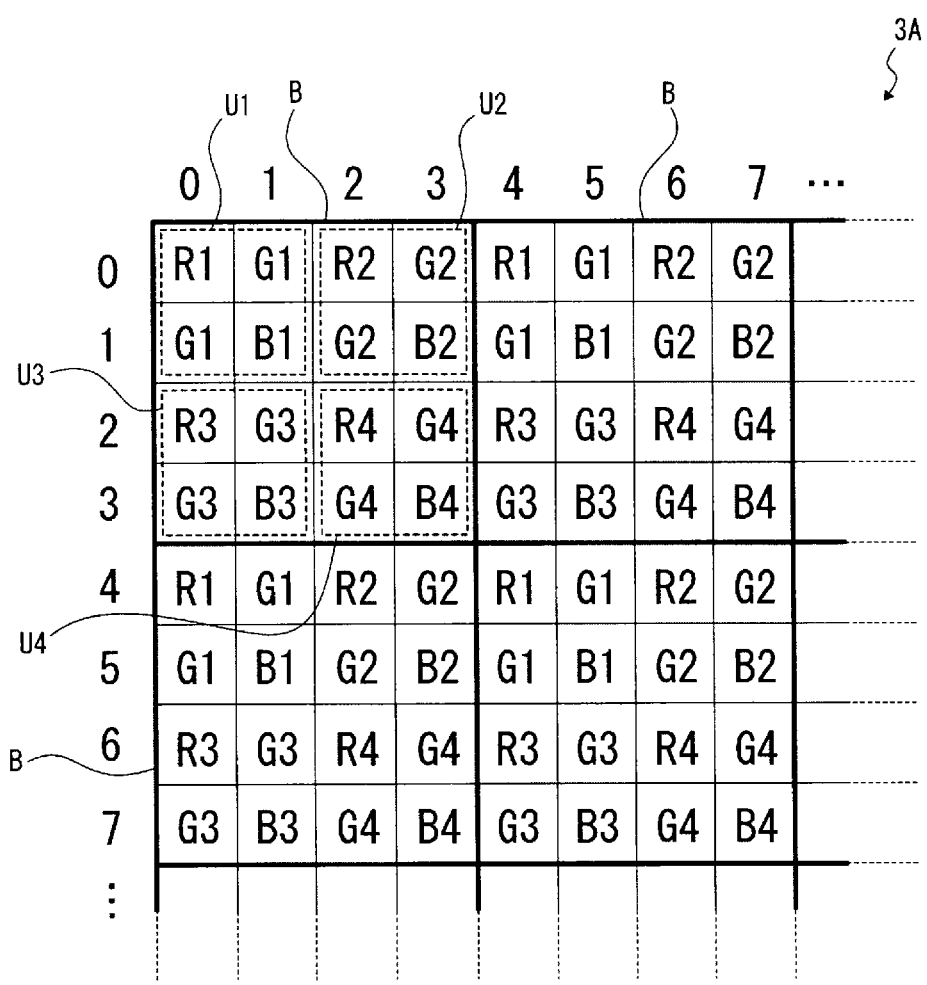

[Fig. 11]
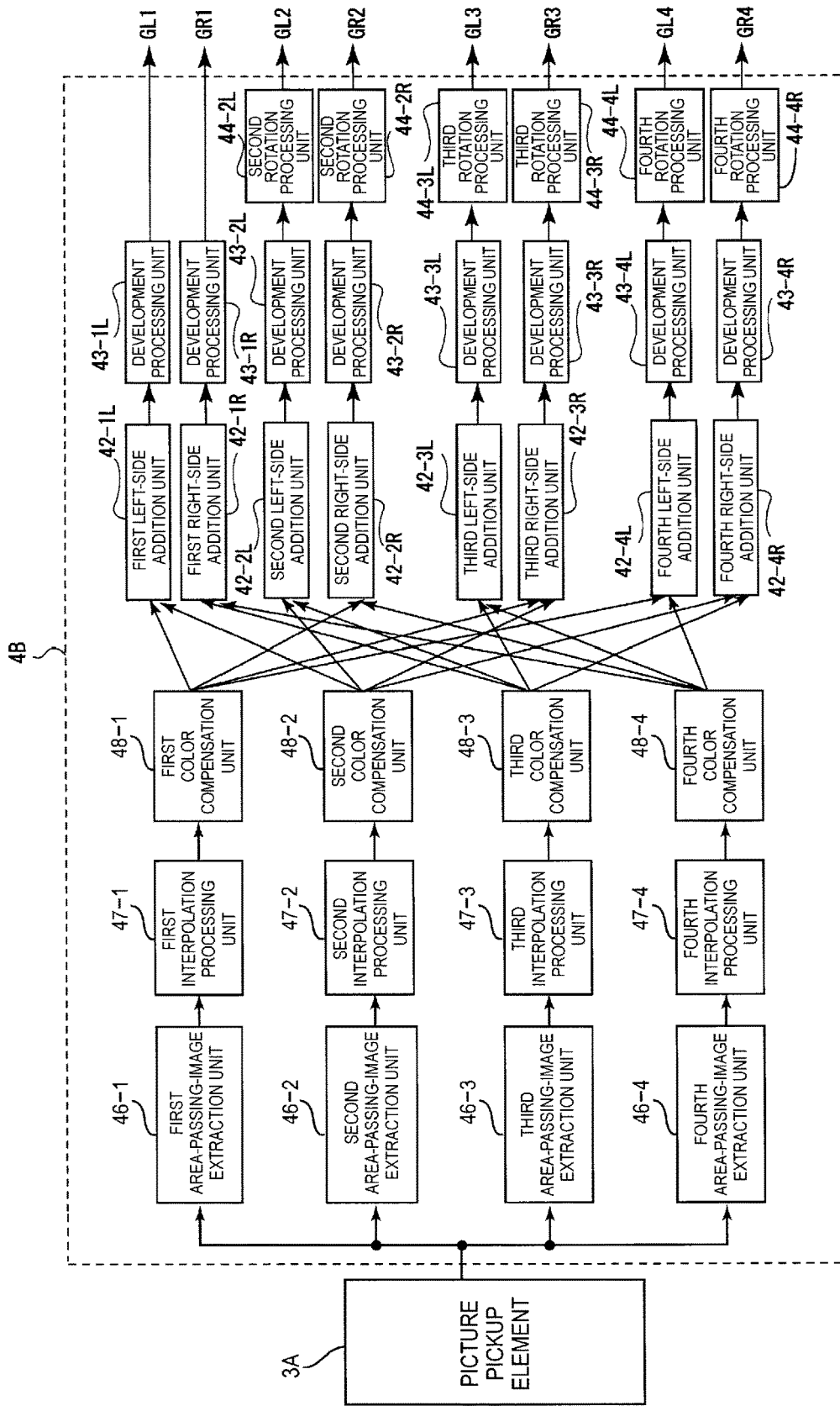

[Fig. 12]
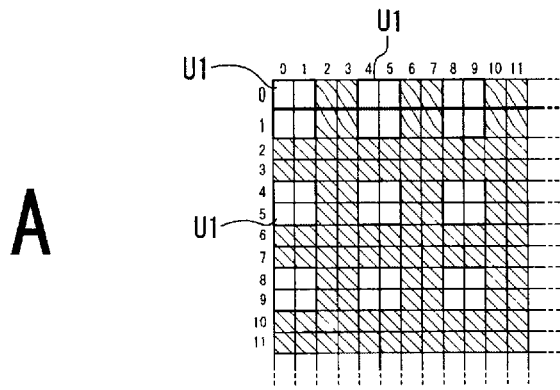
A
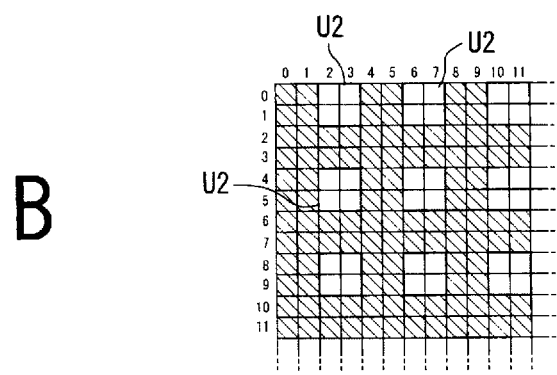
B
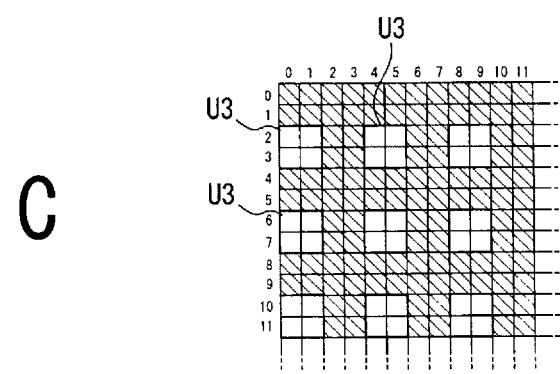
C
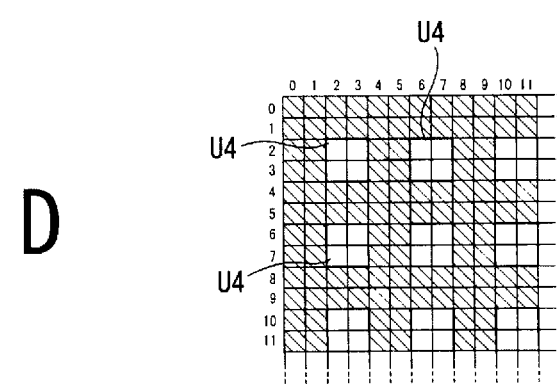
D

[Fig. 13]
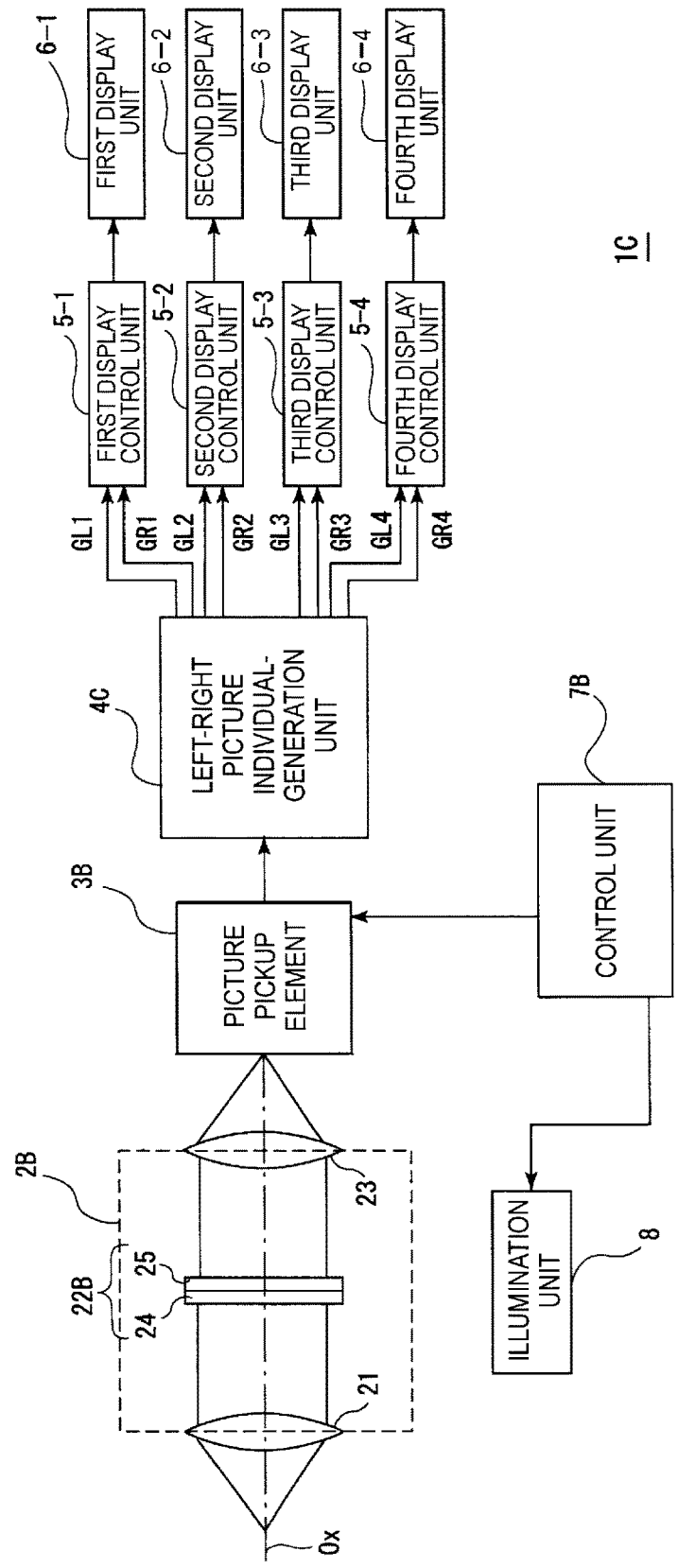

[Fig. 14]
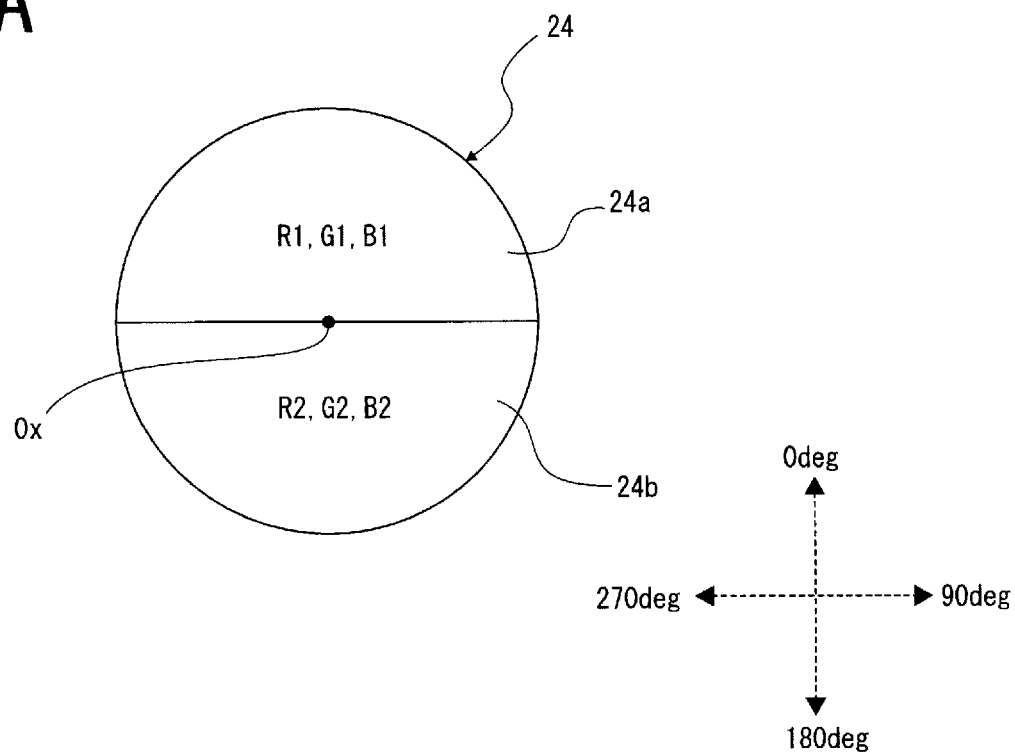
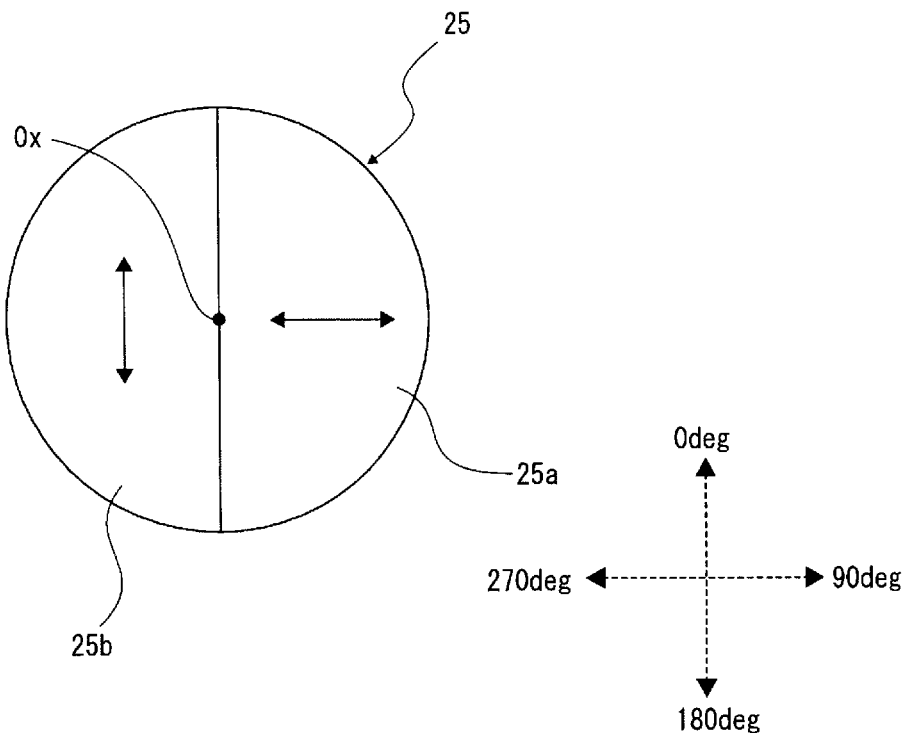

[Fig. 15]
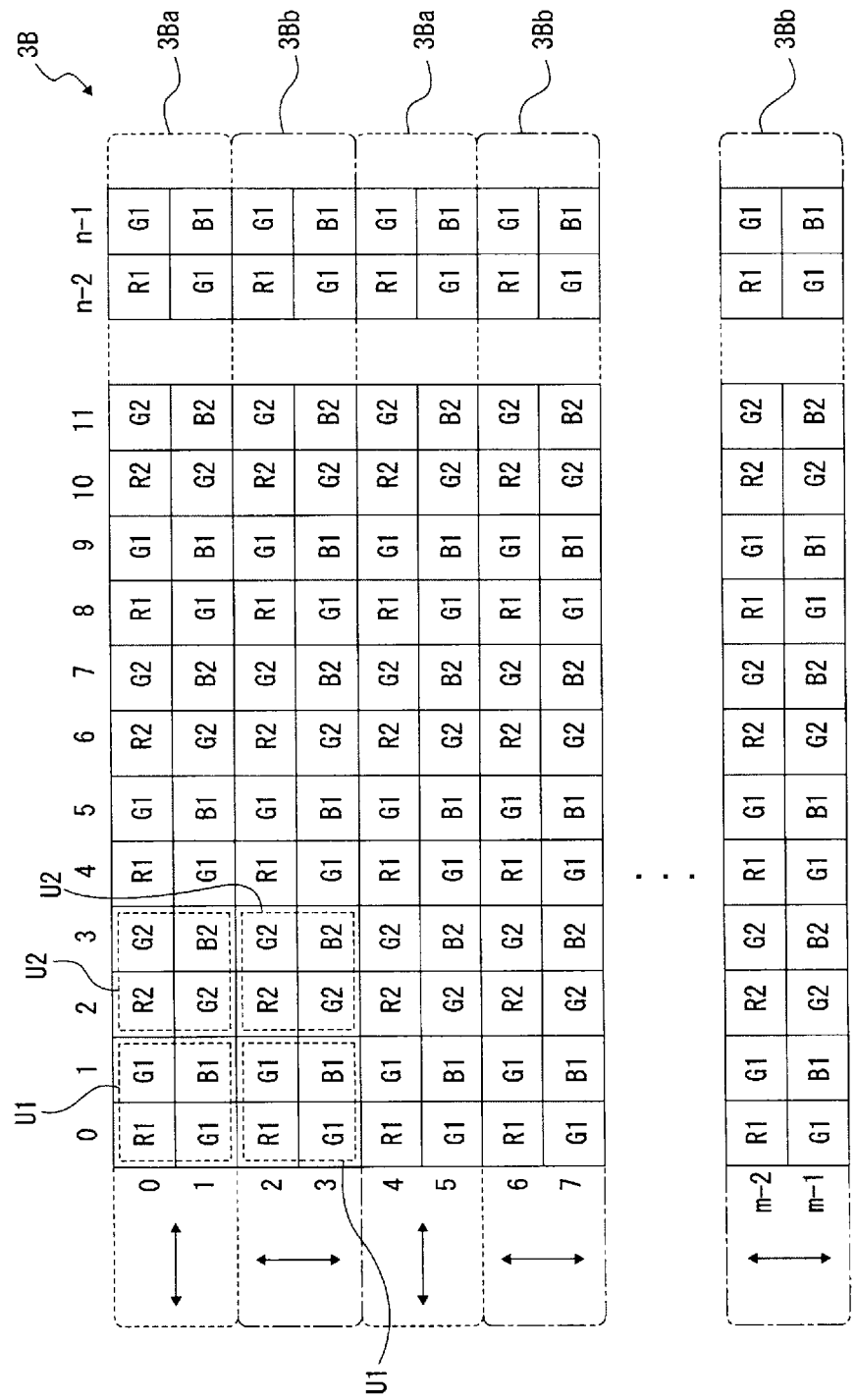

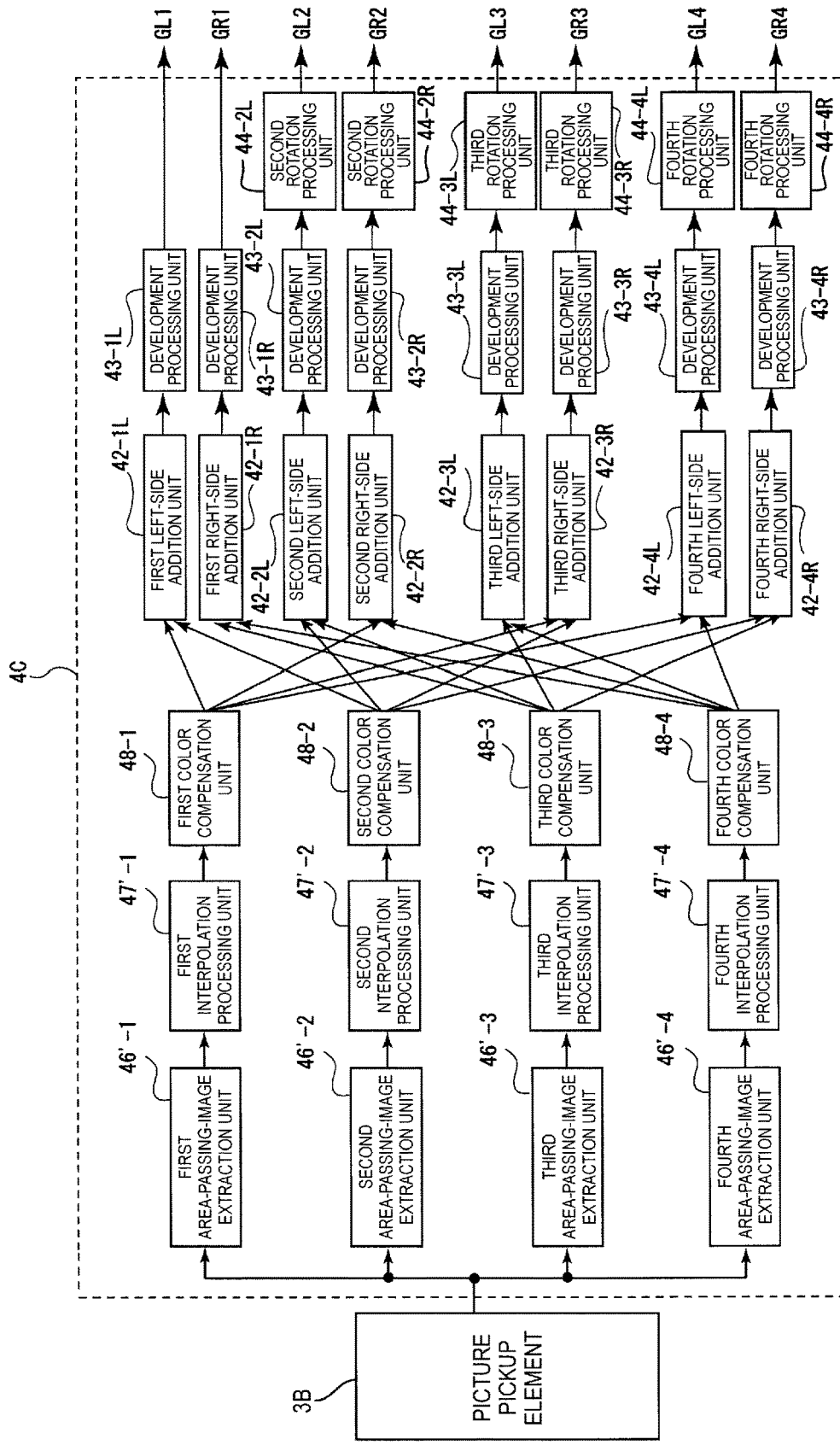
[Fig. 16]

[Fig. 17]
A 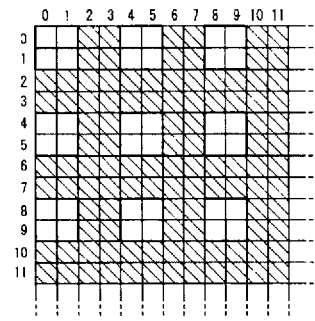
B 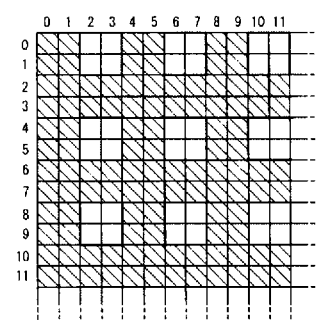
C 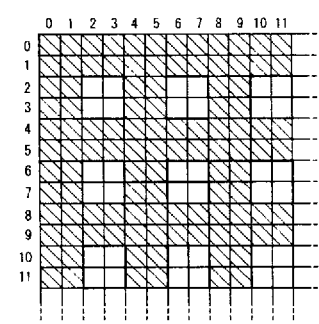
D 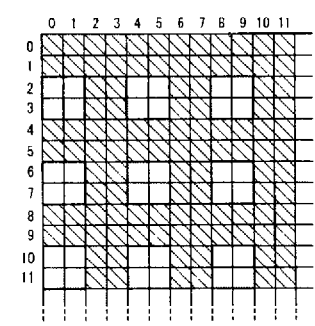

[Fig. 18]
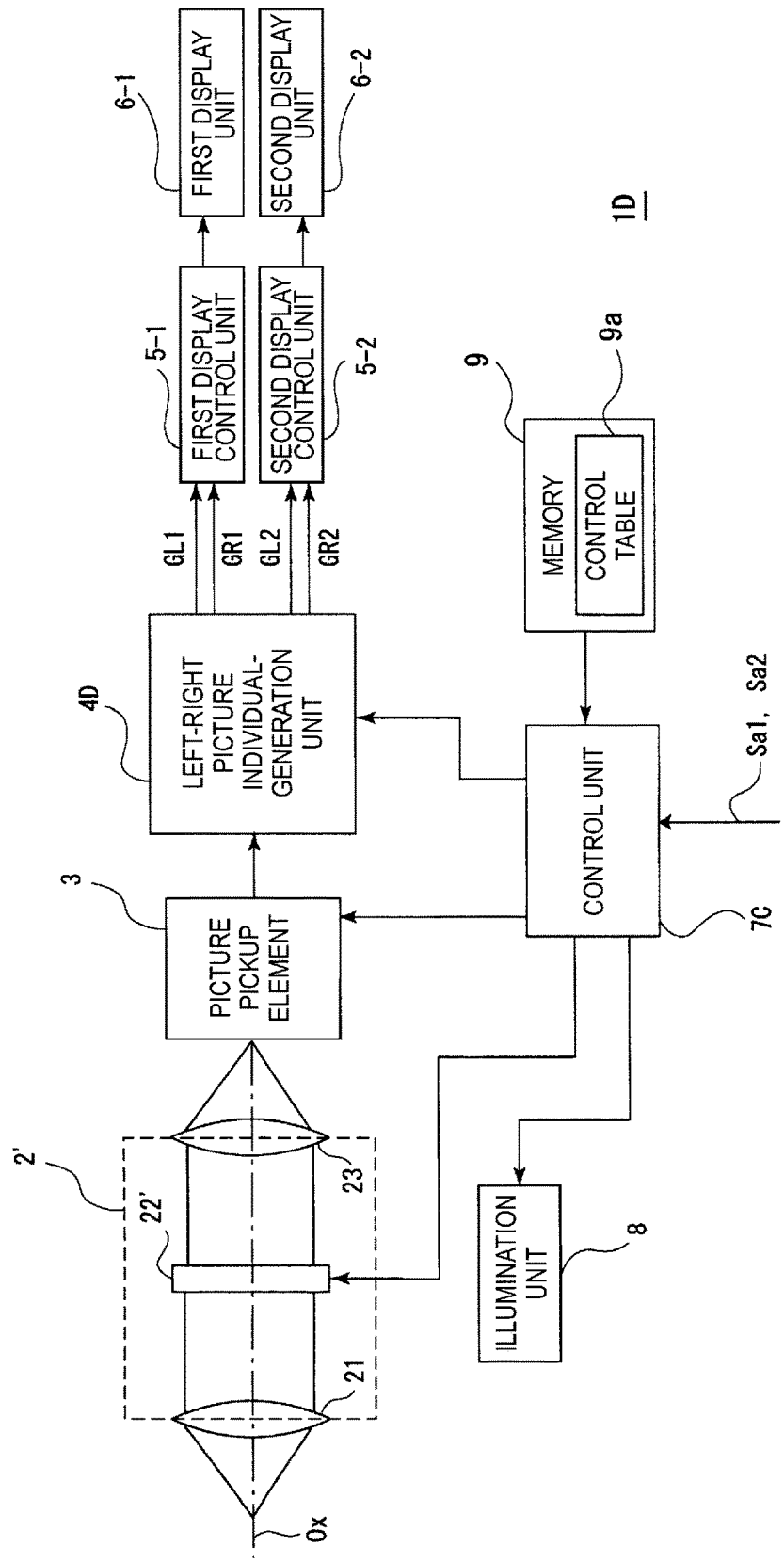

[Fig. 19]
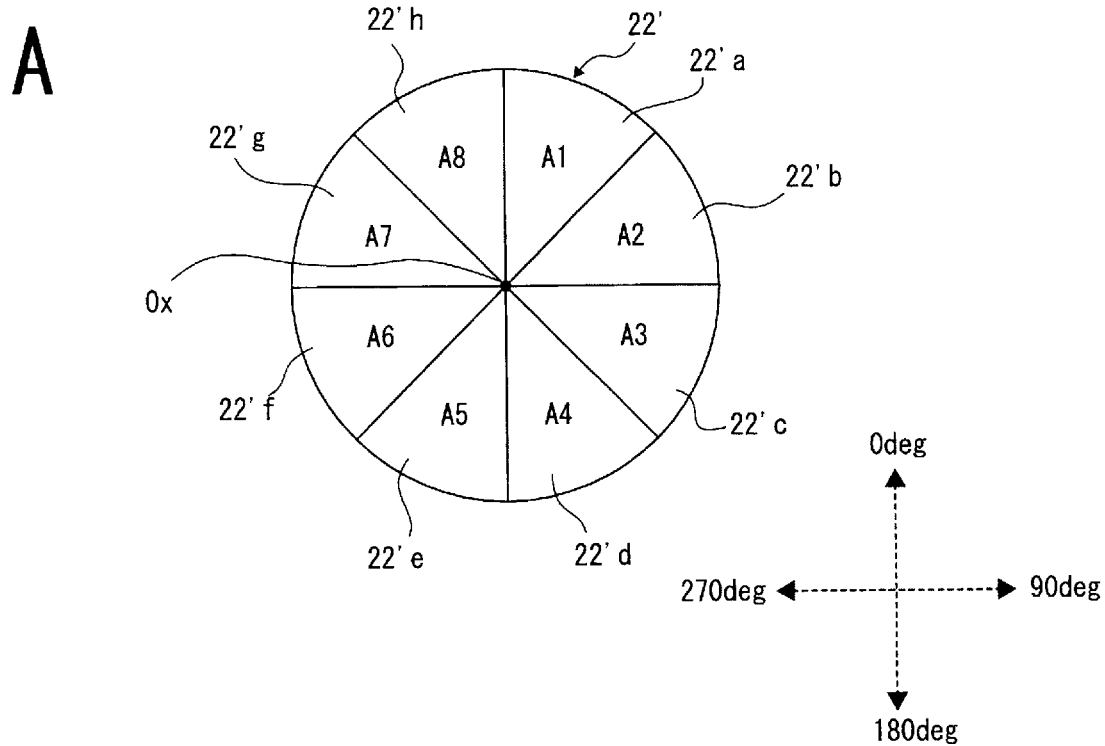
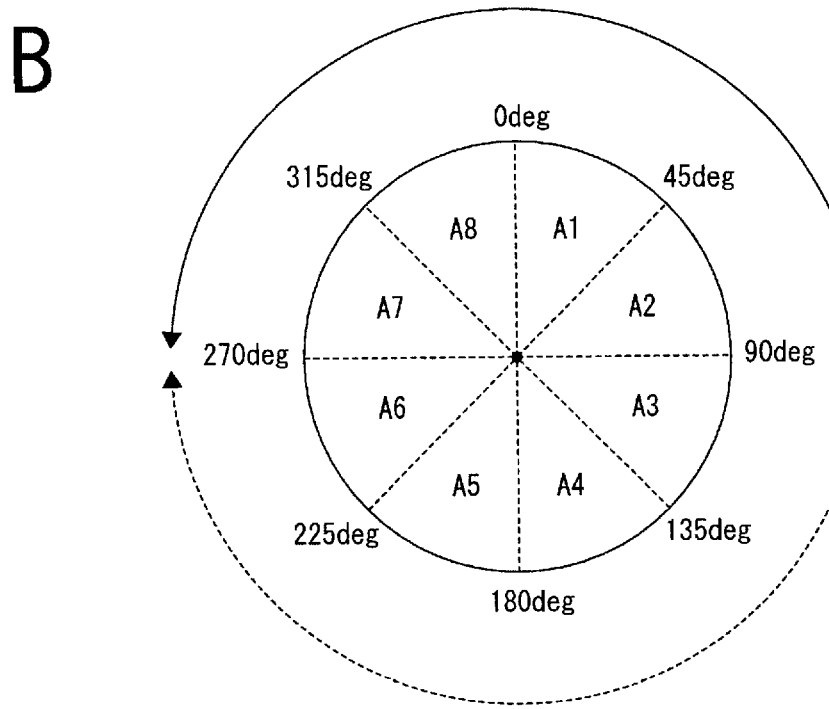

[Fig. 20]
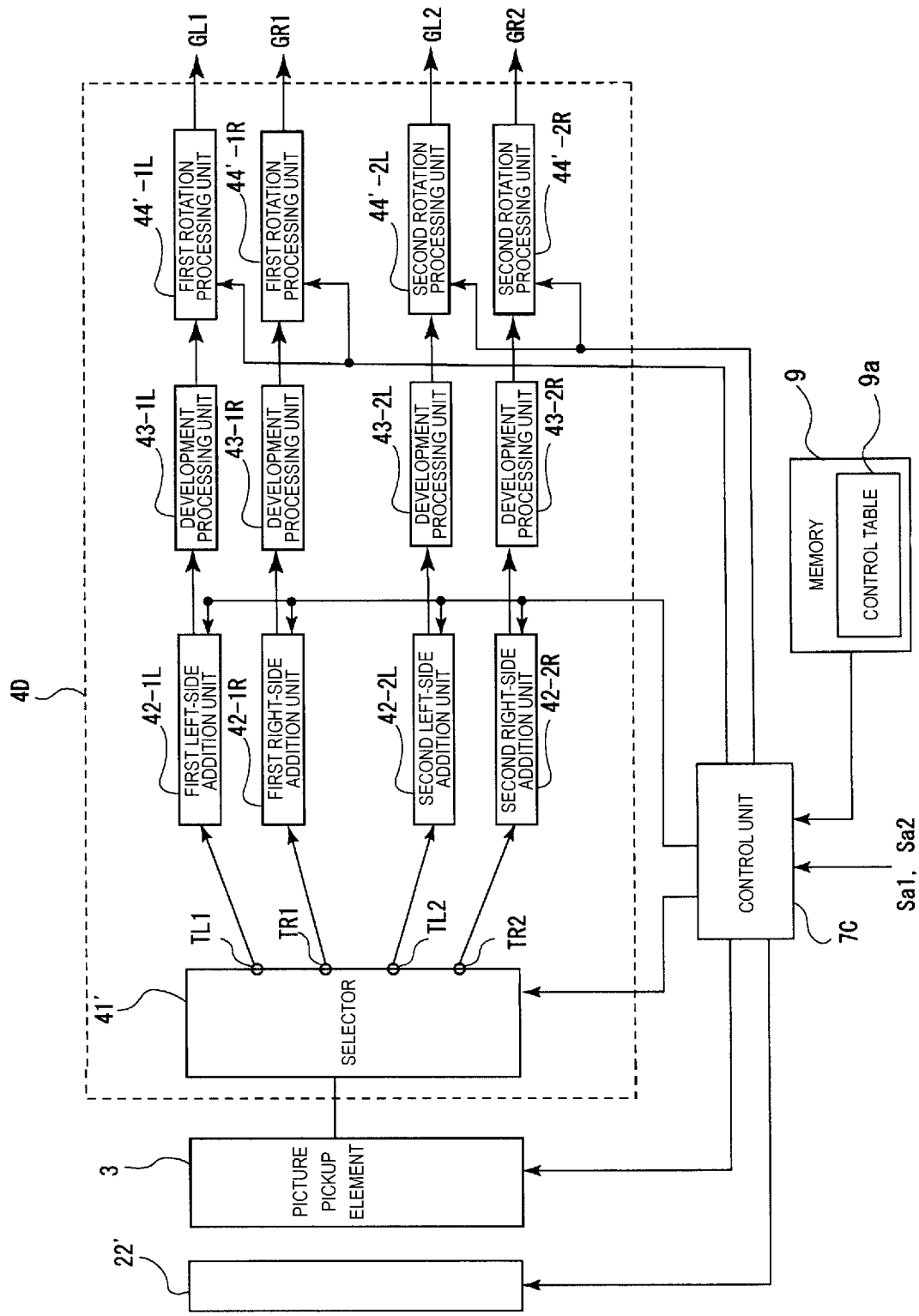

[Fig. 21]
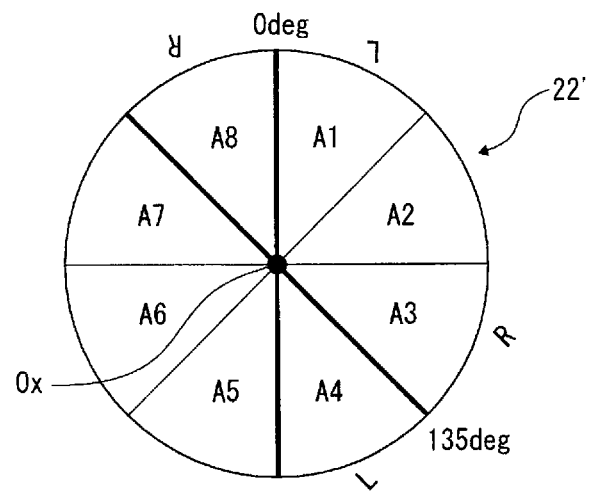
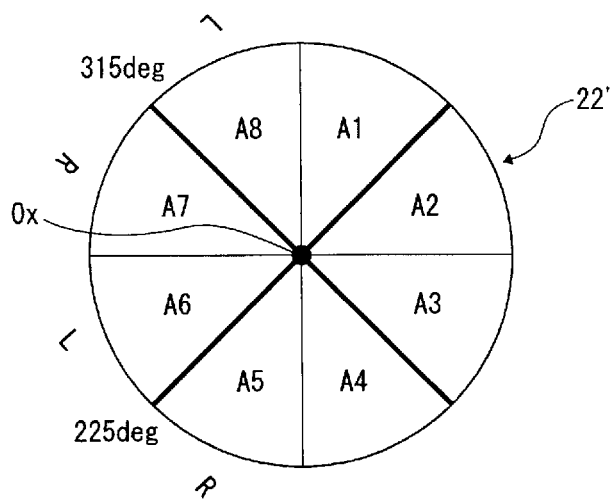
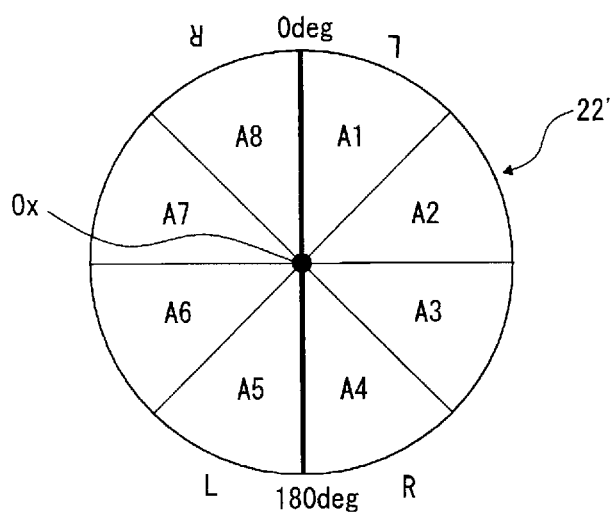

[Fig. 22]
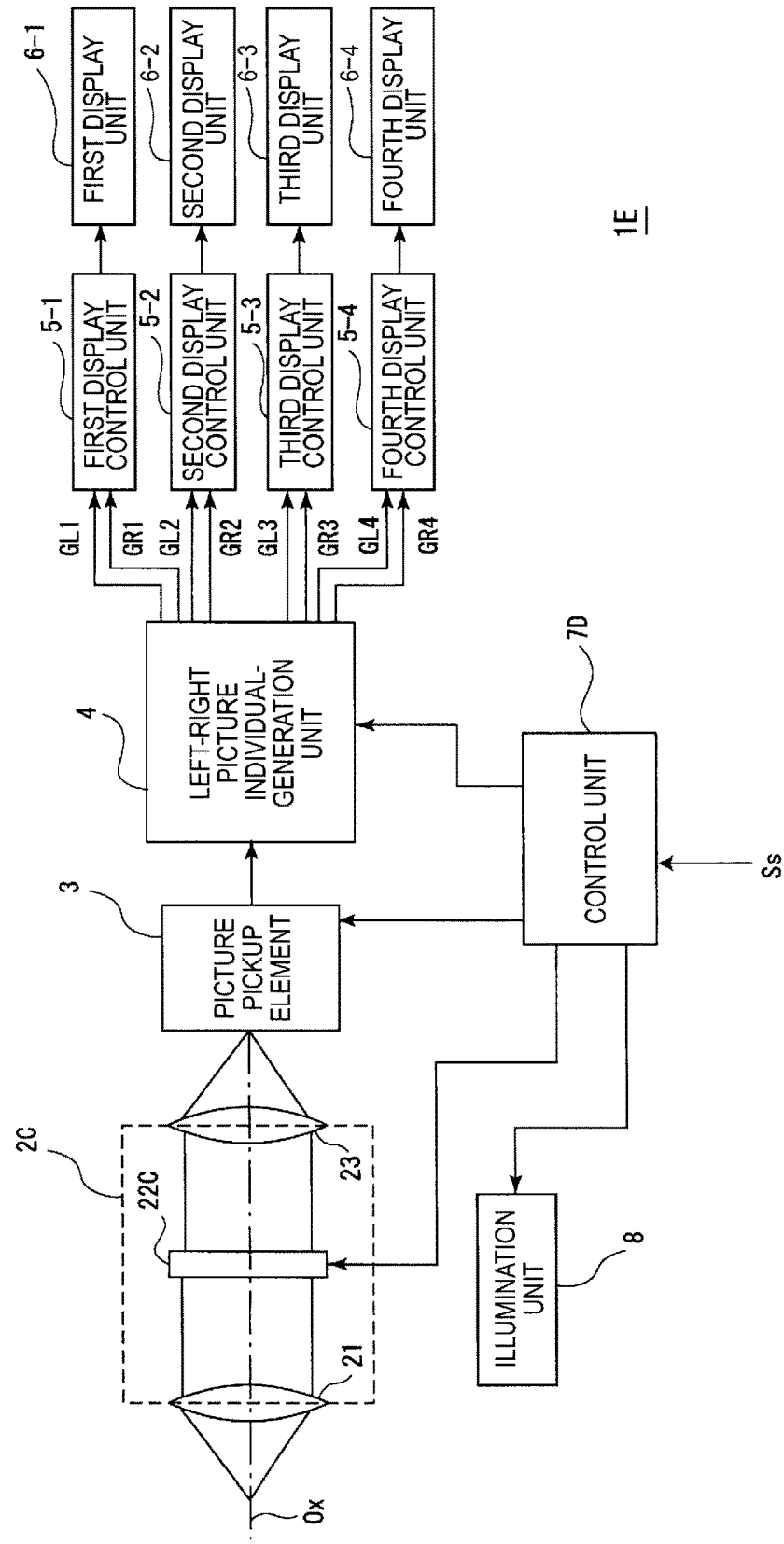

[Fig. 23]
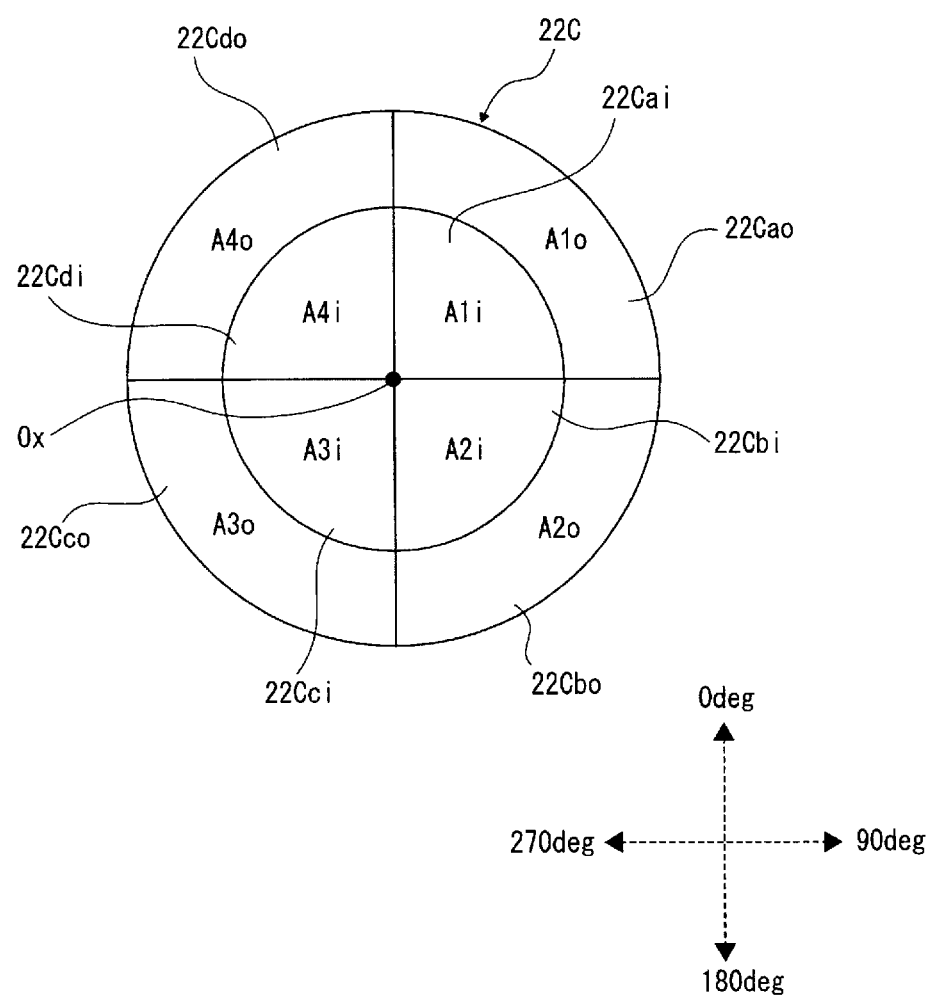

[Fig. 24]
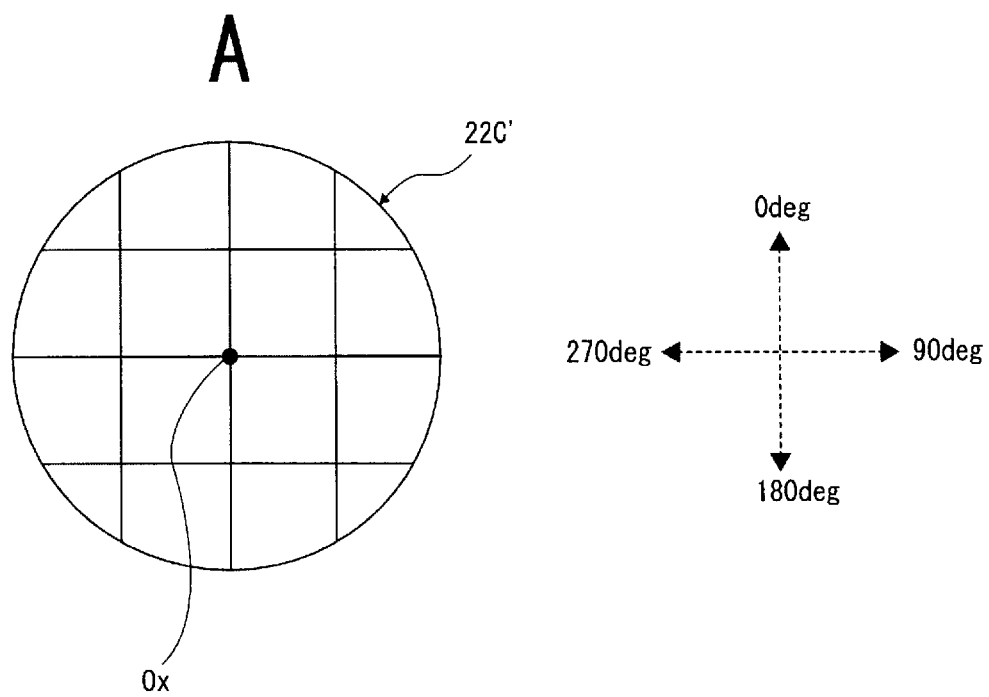
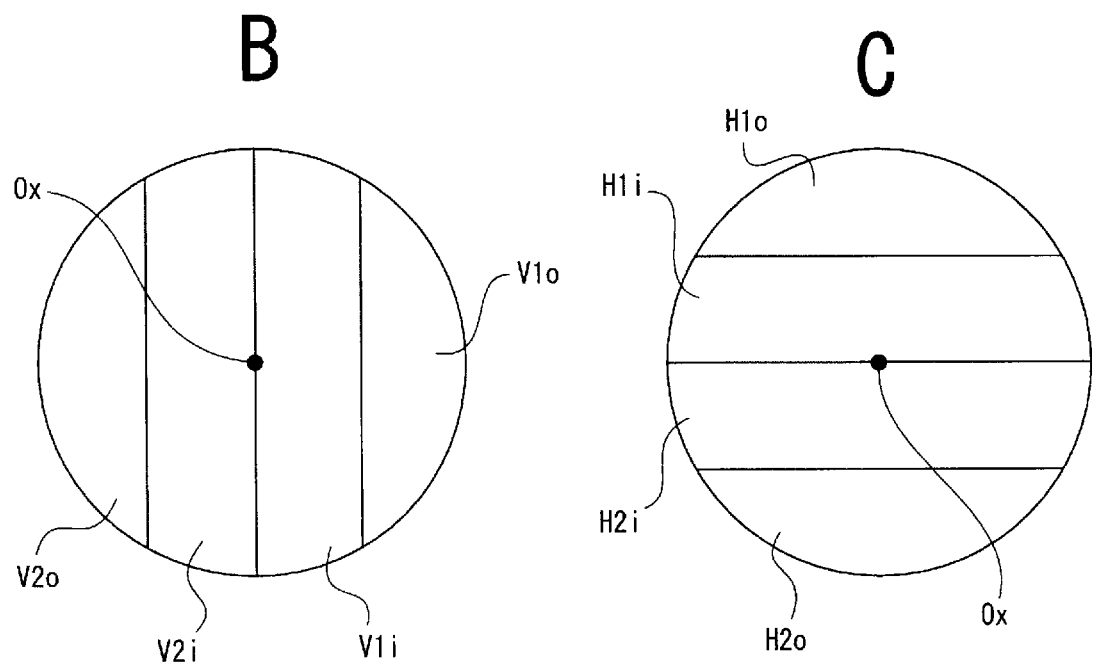

[Fig. 25]
A 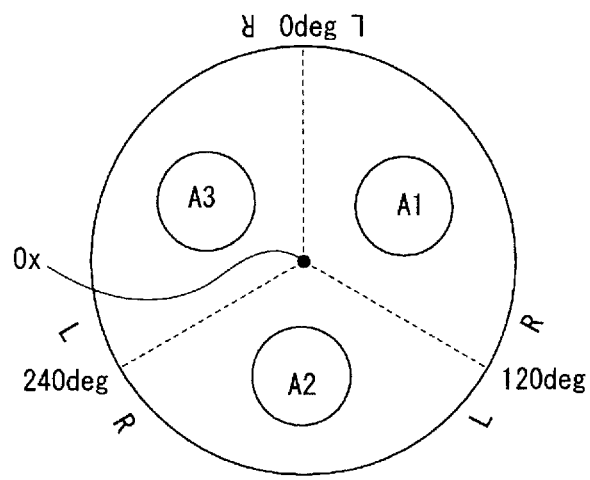
B 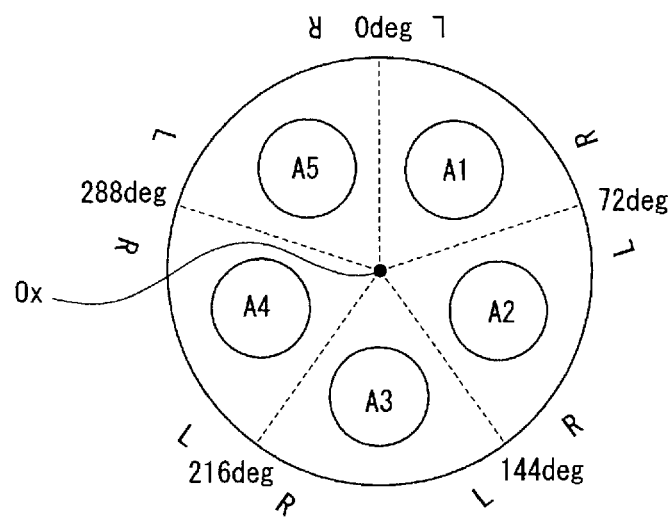

STEREOSCOPIC PICTURE GENERATION APPARATUS AND STEREOSCOPIC PICTURE GENERATION METHOD

CROSS REFERENCE TO RELATED APPLICATIONS

This application claims the benefit of Japanese Priority Patent Application JP 2013-188377 filed Sep. 11, 2013, the entire contents of which are incorporated herein by reference.

TECHNICAL FIELD

The present technology relates to a technical field of a stereoscopic picture generation apparatus for generating a stereoscopic picture and a method therefor.

BACKGROUND ART

There is an operation microscope that is used in, for example, surgical operations, and can present a stereoscopic picture for an observed subject (see PTL 1, for example). For obtaining the stereoscopic picture, it is necessary to individually obtain a left-eye picture corresponding to a picture of the subject viewed by the left eye and a right-eye picture corresponding to a picture viewed by the right eye. The left-eye picture is presented to the left eye of an observer, and the right-eye picture is presented to the right eye. Thereby, the stereoscopic vision is actualized.

PTL 1 discloses a technology that, when a plurality of observers, for example, an operator such as an operating surgeon and his assistants, observe a subject through monitors from different angle directions respectively, generates pictures corresponding to the angle directions of the positions of the respective observers. The "angle direction" mentioned here means a radial angle direction centering on the subject, which is defined as 0 deg (degree) to 360 deg.

Concretely, the technology described in PTL 1 allows the respective observers to perform the observation from arbitrary angle directions, by a plurality of stereoscopic monitors 48 attached so as to be rotatable around a mirror body 12 in which an optical system such as an objective lens 32 is incorporated. The information about the rotation position (angle) of the stereoscopic monitor 48 is input as the information about the angle direction of the position of the observer, and the stereoscopic monitor 48 presents a picture corresponding to the angle direction, that is, a stereoscopic picture by a picture observed from the viewpoint of the left eye of the observer and a picture observed from the viewpoint of the right eye when the observer views the subject from the angle direction.

At this time, for supporting the observation from the plurality of angle directions, the technology described in PTL 1 makes it possible to individually pick up the respective images when the subject is viewed from a plurality of areas (viewpoints) by the division in the direction around the optical axis (see FIG. 6 and others in PTL 1). Then, from those pictures picked up on a viewpoint basis, two pictures corresponding to the angle direction of the position of the observer, that is, a picture observed from the viewpoint of the left eye of the observer who is at the position in the angle direction and a picture observed from the viewpoint of the right eye are selected. Then, they are displayed on the stereoscopic monitor 48 as a left-eye picture and a right-eye picture, and thereby the stereoscopic picture is presented.

CITATION LIST

Patent Literature

PTL 1: JP 2006-50320A

SUMMARY

Technical Problem

As described above, the technology described in PTL 1 makes it possible to individually pick up the images that have passed through the respective areas that are formed by the division in the direction around the optical axis, in order to allow for the observation from the plurality of angle directions.

However, in the technology described in PTL 1, for the individual pickup of the images that have passed through the respective areas, a picture pickup optical system and a picture pickup element are provided in each of the areas. This unfortunately leads to an increase in apparatus size.

Hence, it is desirable to prevent an increase in apparatus size, in the case of properly presenting the respective stereoscopic pictures when a subject is observed from different angle directions.

Solution to Problem

According to one aspect of the present technology, there is presented an information processing apparatus, comprising: an image pickup element configured to acquire at least three images of an object, wherein each of the images respectively correspond to a different perspective of the object; and a control unit configured to selectively combine subsets of the images to generate a plurality of stereoscopic images.

According to another aspect of the present technology, there is presented a non-transitory computer readable medium containing instructions which, when executed, cause a processor to perform operations comprising: accessing at least three images of an object, wherein each of the images correspond to a different perspective of the object; and selectively combining subsets of the images to generate a plurality stereoscopic images.

According to yet another aspect of the present technology, there is presented an electronic system, comprising: an optical unit; the stereoscopic image generation device; and a plurality of display units, wherein the stereoscopic image generation device includes an information apparatus comprising: an image pickup element configured to acquire at least three images of an object, wherein each of the images respectively correspond to a different perspective of the object; and a control unit configured to selectively combine subsets of the images to generate a plurality of stereoscopic images.

According to still another aspect of the present technology, there is presented a method of processing information, comprising: accessing at least three images of an object, wherein each of the images correspond to a different perspective of the object; and selectively combining subsets of the images to generate a plurality stereoscopic images.

In each of the above aspects of the present technology, it may further be presented wherein the control unit is further configured to control the image pickup element to acquire the at least three images individually in sequential time periods.

Additionally, in each of the above aspects of the present technology, there may further include: a pupil having at least three shutter regions and configured to pass light to the image pickup element, wherein the control unit is further configured to selectively shutter subsets of the shutter regions to selectively block light.

Additionally, in each of the above aspects of the present technology, it may further be presented wherein the at least three shutter regions are rotationally symmetric.

Additionally, in each of the above aspects of the present technology, it may further be presented wherein the at least three shutter regions comprise at least three inner shutter regions and at least three outer shutter regions, the at least three inner shutter regions are rotationally symmetric, and the at least three outer shutter regions are rotationally symmetric.

Additionally, in each of the above aspects of the present technology, there may further include: a selector configured to determine which of the at least three images correspond to a left-side and a right-side, respectively; and an addition unit configured to add the images corresponding to a left-side to generate a left-eye image and the images corresponding to a right-side to generate a right-eye image, wherein the control unit is further configured to combine the left-eye image and the right-eye image to generate a respective stereoscopic image.

Additionally, in each of the above aspects of the present technology, it may be further presented wherein the plurality of stereoscopic images is at least three stereoscopic images.

Additionally, in each of the above aspects of the present technology, it may be further presented wherein the respective ones of the plurality of stereoscopic images stereoscopic image include a left-eye image and a right-eye image.

Additionally, in each of the above aspects of the present technology, it may be further presented wherein the at least three images are images obtained by a surgical microscope or an endoscope.

In the above aspects, various components may be an independent device or may be a module to be incorporated into other devices.

Advantageous Effects of Invention

According to the present technology, it is possible to prevent an increase in apparatus size, in the case of properly presenting the respective stereoscopic pictures when a subject is observed from different angle directions.

The effect described here is not necessarily limiting, and all effects described in one or more of embodiments of the present disclosure are possible.

BRIEF DESCRIPTION OF DRAWINGS

FIG. 1 is a block diagram showing an internal configuration of a stereoscopic picture generation apparatus according to a first embodiment.

FIG. 2 is an explanatory diagram for the concept of an angle direction.

FIG. 3 is an explanatory diagram for a configuration of a pupil division unit included in the stereoscopic picture generation apparatus according to the first embodiment.

FIG. 4 is an explanatory diagram for an internal configuration of a left-right picture individual-generation unit included in the stereoscopic picture generation apparatus according to the first embodiment.

FIG. 5 is a block diagram showing an internal configuration of a stereoscopic picture generation apparatus according to a second embodiment.

FIG. 6 is an explanatory diagram for a configuration of an illumination unit included in the stereoscopic picture generation apparatus according to the second embodiment and for an example of wavelength band division.

FIG. 7 is an explanatory diagram for a configuration of a pupil division unit included in the stereoscopic picture generation apparatus according to the second embodiment.

FIG. 8 is an explanatory diagram for an internal configuration of a left-right picture individual-generation unit included in the stereoscopic picture generation apparatus according to the second embodiment.

FIG. 9 is a block diagram showing an internal configuration of a stereoscopic picture generation apparatus according to a third embodiment.

FIG. 10 is an explanatory diagram for a configuration of a picture pickup element included in the stereoscopic picture generation apparatus according to the third embodiment.

FIG. 11 is an explanatory diagram for an internal configuration of a left-right picture individual-generation unit included in the stereoscopic picture generation apparatus according to the third embodiment.

FIG. 12 is an explanatory diagram for pixel positions for which a first area-passing-image extraction unit to a fourth area-passing-image extraction unit according to the third embodiment perform extractions.

FIG. 13 is a block diagram showing an internal configuration of a stereoscopic picture generation apparatus according to a fourth embodiment.

FIG. 14 is an explanatory diagram for configurations of a wavelength separation element and a polarization separation element.

FIG. 15 is an explanatory diagram for a configuration of a picture pickup element included in the stereoscopic picture generation apparatus according to the fourth embodiment.

FIG. 16 is an explanatory diagram for an internal configuration of a left-right picture individual-generation unit included in the stereoscopic picture generation apparatus according to the fourth embodiment.

FIG. 17 is an explanatory diagram for pixel positions for which a first area-passing-image extraction unit to a fourth area-passing-image extraction unit according to the fourth embodiment perform extractions.

FIG. 18 is a block diagram showing an internal configuration of a stereoscopic picture generation apparatus according to a fifth embodiment.

FIG. 19 is an explanatory diagram for a configuration of a pupil division unit included in the stereoscopic picture generation apparatus according to the fifth embodiment and for the movable range of an observer.

FIG. 20 is an explanatory diagram for an internal configuration of a left-right picture individual-generation unit included in the stereoscopic picture generation apparatus according to the fifth embodiment.

FIG. 21 is an explanatory diagram for combinations of areas which light can simultaneously pass.

FIG. 22 is a block diagram showing an internal configuration of a stereoscopic picture generation apparatus according to a sixth embodiment.

FIG. 23 is an explanatory diagram for a configuration of a pupil division unit included in the stereoscopic picture generation apparatus according to the sixth embodiment.

FIG. 24 is an explanatory diagram for a modification of parallax adjustment.

FIG. 25 is an explanatory diagram for modifications of the area division in the pupil division unit.

DESCRIPTION OF EMBODIMENTS

Hereinafter, embodiments will be explained in the following order.
<1. First Embodiment>
<1-1. Overall Configuration of Stereoscopic Picture Generation Apparatus>
<1-2. Time Division Acquisition of Pickup Picture>
<1-3. Generation of Left-Eye Picture and Right-Eye Picture for Each Angle Direction>
<1-4. Summary of First Embodiment><2. Second Embodiment>
<2-1. Configuration and Operation>
<2-2. Summary of Second Embodiment>
<3. Third Embodiment>
<3-1. Configuration and Operation>
<3-2. Summary of Third Embodiment>
<4. Fourth Embodiment>
<4-1. Configuration and Operation>
<4-2. Summary of Fourth Embodiment>
<5. Fifth Embodiment>
<5-1. Configuration and Operation>
<5-2. Summary of Fifth Embodiment>
<6. Sixth Embodiment>
<6-1. Configuration and Operation>
<6-2. Summary of Sixth Embodiment>
<7. Modification>
<8. The Present Technology>

1. First Embodiment

1-1. Overall Configuration of Stereoscopic Picture Generation Apparatus

FIG. 1 is a block diagram showing an internal configuration of a stereoscopic picture generation apparatus 1 according to a first embodiment of the present technology. The stereoscopic picture generation apparatus 1 according to the embodiment, which is, for example, an operation microscope, includes four display units (a first display unit 6-1 to a fourth display unit 6-4) for presenting stereoscopic pictures for an observation subject X to observers. These four display units allow the stereoscopic pictures for the subject X to be simultaneously presented to four observers. In the embodiment, the attachment positions of the first display unit 6-1 to the fourth display unit 6-4 are each fixed. That is, it is assumed that the angle direction of the position of each observer is fixed.

Now, the concept of the "angle direction" in the specification is explained with reference to FIG. 2. First, as shown in FIG. 2A, the "angle direction" mentioned herein means a radial angle direction centering on the subject X, which is defined as 0 deg (degree) to 360 deg. Here, the increasing direction of the angle value (deg) indicating the angle direction matches the clockwise direction when the subject X is viewed from straight above.

FIG. 2B shows a positional relation of the left eye (L) and right eye (R) of an observer relative to the subject X when the observer observes the subject X from the angle direction of 0 deg. Similarly, FIG. 2C to FIG. 2E show positional relations of the left eye and right eye of the observer relative to the subject X when the observer observes the subject X from the angle directions of 90 deg, 180 deg and 270 deg, respectively.

As understood with reference to FIG. 2B to FIG. 2E, the difference in the angle direction of the position of the observer leads to the difference in the positional relation of the left eye and right eye of the observer relative to the subject X.

In the stereoscopic picture generation apparatus 1 according to the embodiment, the first display unit 6-1 is fixed such that the display surface is oriented in the angle direction of 0 deg, and the second display unit 6-2 is fixed such that the display surface is oriented in the angle direction of 90 deg. Further, the third display unit 6-3 is fixed such that the display surface is oriented in the angle direction of 180 deg, and the fourth display unit 6-4 is fixed such that the display surface is oriented in the angle direction of 270 deg.

That is, in this case, the standing position of the observer is in either angle direction of 0 deg, 90 deg, 180 deg and 270 deg.

The explanation returns to FIG. 1.

In FIG. 1, in addition to the above first display unit 6-1 to fourth display unit 6-4, the stereoscopic picture generation apparatus 1 includes an optical unit 2, a picture pickup element 3, a left-right picture individual-generation unit 4, a first display control unit 5-1 to a fourth display control unit 5-4, a control unit 7 and an illumination unit 8.

In the optical unit 2, a condensing lens 21, a pupil division unit 22, and an imaging lens 23 are arranged in that order from the body side (photographic subject side).

The condensing lens 21 condenses light from the subject X that is a photographic subject.

The pupil division unit 22 is provided at such a position that the light condensed by the condensing lens 21 becomes roughly parallel light, and the light through the condensing lens 21 enters the pupil division unit 22.

FIG. 3 is an explanatory diagram for a configuration of the pupil division unit 22. In this figure, the pupil division unit 22 is viewed from the image surface side.

The pupil division unit 22, in which a plurality of areas A are formed by division in the direction around the optical axis Ox, can allow incident light to pass through the areas A/block incident light for each of the areas A. Concretely, the pupil division unit 22 according to the embodiment is divided into four areas A, by two dividing lines (pupil dividing lines) that intersect with the optical axis Ox.

FIG. 3 shows the relation between the pupil division unit 22 and the angle direction, by additionally writing the angle directions on the basis of the subject X. As shown in the figure, one dividing line is parallel to the 0 deg-180 deg axis and the other dividing line is parallel to the 90 deg-270 deg axis, so that the four areas A are even areas. Of the four areas A, an area A of 0 deg to 90 deg is referred to as an "area A1", an area A of 90 deg to 180 deg is referred to as an "area A2", an area A of 180 deg to 270 deg is referred to as an "area A3", and an area A of 270 deg to 0 deg (360 deg) is referred to as an "area A4".

Each of the areas A is constituted by an electronic shutter, and thereby the pupil division unit 22 can allow incident light to pass through the areas A/block incident light for each of the areas A. The electronic shutters formed in the areas A1, A2, A3 and A4 are referred to as the "first electronic shutter 22a", the "second electronic shutter 22b", the "third electronic shutter 22c" and the "fourth electronic shutter 22d", respectively.

In the case of an operation microscope, typically, the observation of the subject X is performed with the condensing lens 21 positioned straight above the subject X. In FIGS.

7, 14, 19A, 21, 23, 24 and 25 described later, as well as in FIG. 3, the angle directions are additionally written under this assumption.

The opening/closing control of the first electronic shutter 22a to the fourth electronic shutter 22d in the pupil division unit 22 is performed by the control unit 7.

In FIG. 1, the light that has passed through the pupil division unit 22 is imaged on a picture pickup surface (light receiving surface) of the picture pickup element 3 through the imaging lens 23.

The picture pickup element 3 is constituted by, for example, CCDs (Charge Coupled Devices), a CMOS (Complementary Metal Oxide Semiconductor) image sensor, or the like, and on a pixel basis, receives the light corresponding to a photographic subject image formed on the picture pickup surface, to convert it into an electric signal (photoelectric conversion). In the embodiment, the picture pickup element 3 is a so-called RGGB-type picture pickup element, and allows for picture pickup of a color picture.

In the embodiment, the placement angle of the picture pickup element 3 in the direction around the optical axis Ox is set such that the position where the angle direction is 0 deg is the reference position for observation. Concretely, the placement angle of the picture pickup element 3 in the direction around the optical axis Ox is set such that the orientation of the subject X exhibited in a stereoscopic picture that is presented by the first display unit 6-1, whose display surface is oriented in the angle direction of 0 deg, matches the orientation (see FIG. 2B) of the subject X when an observer at the position in the direction of 0 deg actually observes the subject X.

The left-right picture individual-generation unit 4 generates a left-eye picture GL1, a right-eye picture GR1, a left-eye picture GL2, a right-eye picture GR2, a left-eye picture GL3, a right-eye picture GR3, a left-eye picture GL4 and a right-eye picture GR4, based on the electric signal obtained on a pixel basis by the picture pickup element 3, that is, based on a pickup picture signal. The left-eye picture GL1 and the right-eye picture GR1 are pictures respectively corresponding to an image to be observed by the left eye of an observer at the position in the angle direction of 0 deg and an image to be observed by the right eye of the observer. The left-eye picture GL2 and the right-eye picture GR2 are pictures respectively corresponding to an image to be observed by the left eye of an observer at the position in the angle direction of 90 deg and an image to be observed by the right eye of the observer. The left-eye picture GL3 and the right-eye picture GR3 are pictures respectively corresponding to an image to be observed by the left eye of an observer at the position in the angle direction of 180 deg and an image to be observed by the right eye of the observer. The left-eye picture GL4 and the right-eye picture GR4 are pictures respectively corresponding to an image to be observed by the left eye of an observer at the position in the angle direction of 270 deg and an image to be observed by the right eye of the observer. The internal configuration of the left-right picture individual-generation unit 4 will be described later.

The left-eye picture GL1 and right-eye picture GR1 generated by the left-right picture individual-generation unit 4 are supplied to the first display control unit 5-1, the left-eye picture GL2 and right-eye picture GR2 are supplied to the second display control unit 5-2, the left-eye picture GL3 and right-eye picture GR3 are supplied to the third display control unit 5-3, and the left-eye picture GL4 and right-eye picture GR4 are supplied to the fourth display control unit 5-4.

The first display control unit 5-1 performs a control for displaying the left-eye picture GL and right-eye picture GR supplied from the left-right picture individual-generation unit 4, on the first display unit 6-1, such that the stereoscopic vision is actualized. Similarly, the second display control unit 5-2, the third display control unit 5-3 and the fourth display control unit 5-4 respectively perform controls for displaying the left-eye pictures GL and right-eye pictures GR supplied from the left-right picture individual-generation unit 4, on the second display unit 6-2, the third display unit 6-3 and the fourth display unit 6-4, such that the stereoscopic visions are actualized. In the embodiment, for example, the first display unit 6-1 to the fourth display unit 6-4 are display devices to present a stereoscopic picture by a lenticular technique, and each display control units 5 performs a display control compatible with the lenticular technique.

Here, at least one of the first display unit 6-1 to the fourth display unit 6-4 may be a glasses-type display device. In this case, a display unit 6 that is a glasses-type display device is connected with the main unit of the stereoscopic picture generation apparatus 1 through a cable, or is display-controlled by the corresponding display control unit 5 through wireless communication.

The illumination unit 8 includes, for example, a light source to emit visible light such as white color, and puts on the light source to illuminate the subject X, in response to the instruction from the control unit 7.

For example, the control unit 7 is constituted by a microcomputer including a CPU (Central Processing Unit) and memories such as a ROM (Read Only Memory) and a RAM (Random Access Memory), and the CPU executes processes in accordance with programs recorded in the ROM, for example, and thereby, controls the whole of the stereoscopic picture generation apparatus 1.

For example, the control unit 7 performs the opening/closing control of the first electronic shutter 22a to the fourth electronic shutter 22d of the pupil division unit 22. Further, the control unit 7 controls the picture pickup operation by the picture pickup element 3. In addition, the control unit 7 controls the left-right picture individual-generation unit 4.

Concrete contents of these controls by the control unit 7 for the first electronic shutter 22a to the fourth electronic shutter 22d, the picture pickup element 3 and the left-right picture individual-generation unit 4 will be described later.

1-2. Time Division Acquisition of Pickup Picture

As shown in FIG. 3, the stereoscopic picture generation apparatus 1 according to the embodiment, using the pupil division unit 22 that can allow incident light to pass through the areas A/block incident light for each of the areas A, alternately forms pictures on the picture pickup element 3 for an image that has passed through the area A1, an image that has passed through the area A2, an image that has passed through the area A3 and an image that has passed through the area A4. Concretely, the first electronic shutter 22a, the second electronic shutter 22b, the third electronic shutter 22c and the fourth electronic shutter 22d are opened sequentially and alternately, and thereby, for the image that has passed through the area A1, the image that has passed through the area A2, the image that has passed through the area A3 and the image that has passed through the area A4, the pictures are formed on the picture pickup element 3, individually in the time axis direction.

Here, comparing the foregoing FIG. 2 and FIG. 3, it is found that the area A1 constitutes a part of the left-eye area when the subject X is observed from the angle direction of 0 deg. Further, it is found that, at the same time, the area A1 constitutes a part of the right-eye area when the subject X is observed from the angle direction of 90 deg, a part of the right-eye area when the subject X is observed from the angle direction of 180 deg, and a part of the left-eye area when the subject X is observed from the angle direction of 270 deg. As understood in this regard, each area A of the area A1 to the area A4 constitutes a part of the left-eye area or right-eye area when the subject X is observed from an arbitrary angle direction of 0 deg, 90 deg, 180 deg and 270 deg.

For confirmation, the left-eye areas and right-eye areas for the respective observers at the positions in the angle directions of 0 deg, 90 deg, 180 deg and 270 deg are shown as follows.

0 deg
Left-eye area . . . A1+A2
Right-eye area . . . A3+A4
90 deg
Left-eye area . . . A2+A3
Right-eye area . . . A1+A4
180 deg
Left-eye area . . . A3+A4
Right-eye area . . . A1+A2
270 deg
Left-eye area . . . A1+A4
Right-eye area . . . A2+A3

From the above, it is found that by combining the images that have passed through the area A1, the area A2, the area A3 and the area A4 in a predetermined manner corresponding to the angle directions of 0 deg, 90 deg, 180 deg and 270 deg, it is possible to acquire the left-eye pictures GL and right-eye pictures GR corresponding to the respective angle directions.

The control unit 7 executes, repeatedly in a predetermined cycle, such a control that the first electronic shutter 22a, the second electronic shutter 22b, the third electronic shutter 22c and the fourth electronic shutter 22d are opened sequentially and alternately.

Here, a period during which incident light passes through only the area A1 is referred to as a "period t1", a period during which incident light passes through only the area A2 is referred to as a "period t2", a period during which incident light passes through only the area A3 is referred to as a "period t3", and a period during which incident light passes through only the area A4 is referred to as a "period t4".

The control unit 7 controls the picture pickup operation of the picture pickup element 3 such that the picture pickup element 3 individually acquires the pickup picture signal in each of the period t1 to the period t4.

Thereby, in the picture pickup element 3, a pickup picture signal for the image that has passed through the area A1 (referred to as a "pickup picture signal Ga1"), a pickup picture signal for the image that has passed through the area A2 (referred to as a "pickup picture signal Ga2"), a pickup picture signal for the image that has passed through the area A3 (referred to as a "pickup picture signal Ga3"), and a pickup picture signal for the image that has passed through the area A4 (referred to as a "pickup picture signal Ga4") are acquired individually in the time axis direction.

1-3. Generation of Left-Eye Picture and Right-Eye Picture for Each Angle Direction FIG. 4 is an explanatory diagram for an internal configuration of the left-right picture individual-generation unit 4. This figure additionally shows the picture pickup element 3 and the control unit 7, also.

The left-right picture individual-generation unit 4 includes a selector 41, a first left-side addition unit 42-1L, a first right-side addition unit 42-1R, a second left-side addition unit 42-2L, a second right-side addition unit 42-2R, a third left-side addition unit 42-3L, a third right-side addition unit 42-3R, a fourth left-side addition unit 42-4L, a fourth right-side addition unit 42-4R, a development processing unit 43-1L, a development processing unit 43-1R, a development processing unit 43-2L, a development processing unit 43-2R, a development processing unit 43-3L, a development processing unit 43-3R, a development processing unit 43-4L, a development processing unit 43-4R, a second rotation processing unit 44-2L, a second rotation processing unit 44-2R, a third rotation processing unit 44-3L, a third rotation processing unit 44-3R, a fourth rotation processing unit 44-4L, and a fourth rotation processing unit 44-4R.

To the selector 41, the pickup picture signals Ga1 to Ga4 are sequentially input by the picture pickup element 3. The selector 41 includes output terminals TL1, TR1, TL2, TR2, TL3, TR3, TL4 and TR4. As shown in the figure, the output terminal TL1 is connected with the first left-side addition unit 42-1L, and the output terminal TR1 is connected with the first right-side addition unit 42-1R. Further, the output terminal TL2 is connected with the second left-side addition unit 42-2L, the output terminal TR2 is connected with the second right-side addition unit 42-2R, the output terminal TL3 is connected with the third left-side addition unit 42-3L, the output terminal TR3 is connected with the third right-side addition unit 42-3R, the output terminal TL4 is connected with the fourth left-side addition unit 42-4L, and the output terminal TR4 is connected with the fourth right-side addition unit 42-4R.

The selector 41 outputs, on a period t basis, the pickup picture signal Ga input from the picture pickup element 3, from the output terminal T selected in response to the instruction from the control unit 7.

On a period t basis, the control unit 7 makes the selector 41 select the output terminal T for outputting the pickup picture signal Ga, as follows.
t1 . . . TL1, TR2, TR3, TL4
t2 . . . TL1, TL2, TR3, TR4
t3 . . . TR1, TL2, TL3, TR4
t4 . . . TR1, TR2, TL3, TL4

Thereby, for the observer at the position in the angle direction of 0 deg, the pickup picture signals Ga1 and Ga2 necessary for obtaining the left-eye picture GL1 are input to the first left-side addition unit 42-1L, and the pickup picture signals Ga3 and Ga4 necessary for obtaining the right-eye picture GR1 are input to the first right-side addition unit 42-1R. Further, for the observer at the position in the angle direction of 90 deg, the pickup picture signals Ga2 and Ga3 necessary for obtaining the left-eye picture GL2 are input to the second left-side addition unit 42-2L, and the pickup picture signals Ga1 and Ga4 necessary for obtaining the right-eye picture GR2 are input to the second right-side addition unit 42-2R. Further, for the observer at the position in the angle direction of 180 deg, the pickup picture signals Ga3 and Ga4 necessary for obtaining the left-eye picture GL3 are input to the third left-side addition unit 42-3L, and the pickup picture signals Ga1 and Ga2 necessary for obtaining the right-eye picture GR3 are input to the third right-side addition unit 42-3R. Further, for the observer at the position in the angle direction of 270 deg, the pickup picture signals Ga1 and Ga4 necessary for obtaining the left-eye picture GL4 are input to the fourth left-side addition unit 42-4L, and the pickup picture signals Ga2 and Ga3 necessary for obtaining the right-eye picture GR4 are input to the fourth right-side addition unit 42-4R.

Each addition unit 42 adds the respective pickup pictures that are based on the two input pickup picture signals.

The pickup picture after the addition by the first left-side addition unit 42-1L is supplied to the development processing unit 43-1L, the pickup picture after the addition by the first right-side addition unit 42-1R is supplied to the development processing unit 43-1R, the pickup picture after the addition by the second left-side addition unit 42-2L is supplied to the development processing unit 43-2L, the pickup picture after the addition by the second right-side addition unit 42-2R is supplied to the development processing unit 43-2R, the pickup picture after the addition by the third left-side addition unit 42-3L is supplied to the development processing unit 43-3L, the pickup picture after the addition by the third right-side addition unit 42-3R is supplied to the development processing unit 43-3R, the pickup picture after the addition by the fourth left-side addition unit 42-4L is supplied to the development processing unit 43-4L, and the pickup picture after the addition by the fourth right-side addition unit 42-4R is supplied to the development processing unit 43-4R.

Each development processing unit 43 performs a development process for the input pickup picture. The development process in the embodiment, in which the RGGB-type picture pickup element 3 is used, is a demosaic process for obtaining the respective values of R, G and B at least for each pixel of the picture pickup element 3. The demosaic process may be a process in which, for a pixel at a horizontally i-th and vertically j-th position on the picture pickup element 3, the values of the colors other than the color to be light-received by the color filter (wavelength filter) of the pixel are calculated respectively using the values of same-color pixels in the vicinity.

By this development process, the pickup picture is obtained as a color picture.

The pickup picture obtained by the development processing unit 43-1L is output as the left-eye picture GL1. Further, the pickup picture obtained by the development processing unit 43-1R is output as the right-eye picture GR1.

Meanwhile, the pickup picture obtained by the development processing unit 43-2L is supplied to the second rotation processing unit 44-2L, the pickup picture obtained by the development processing unit 43-2R is supplied to the second rotation processing unit 44-2R, the pickup picture obtained by the development processing unit 43-3L is supplied to the third rotation processing unit 44-3L, the pickup picture obtained by the development processing unit 43-3R is supplied to the third rotation processing unit 44-3R, the pickup picture obtained by the development processing unit 43-4L is supplied to the fourth rotation processing unit 44-4L, and the pickup picture obtained by the development processing unit 43-4R is supplied to the fourth rotation processing unit 44-4R.

Each rotation processing unit 44 rotates the input pickup picture by a previously determined angle. Concretely, the second rotation processing units 44-2L and 44-2R rotate the input pickup picture by 90 deg. The third rotation processing units 44-3L and 44-3R rotate the input pickup picture by 180 deg. The fourth rotation processing units 44-4L and 44-4R rotate the input pickup picture by 270 deg.

As described above, in the stereoscopic picture generation apparatus 1 according to the embodiment, the placement angle of the picture pickup element 3 in the direction around the optical axis Ox is set such that the position where the angle direction is 0 deg is the reference position for observation. Therefore, the pickup pictures corresponding to the angle directions other than 0 deg are rotated by angles corresponding to the differences from 0 deg, respectively. Thereby, for the observers at the positions in the angle directions other than 0 deg, it is possible to avoid a situation in which the orientation of the subject X exhibited in the stereoscopic picture does not match the orientation of the subject X when the subject X is actually observed.

The pickup picture after the rotation process by the second rotation processing unit 44-2L is output as the left-eye picture GL2, and the pickup picture after the rotation process by the second rotation processing unit 44-2R is output as the right-eye picture GR2. The pickup picture after the rotation process by the third rotation processing unit 44-3L is output as the left-eye picture GL3, and the pickup picture after the rotation process by the third rotation processing unit 44-3R is output as the right-eye picture GR3. The pickup picture after the rotation process by the fourth rotation processing unit 44-4L is output as the left-eye picture GL4, and the pickup picture after the rotation process by the fourth rotation processing unit 44-4R is output as the right-eye picture GR4.

1-4. Summary of First Embodiment

As described above, the stereoscopic picture generation apparatus 1 according to the first embodiment includes the pupil division unit 22 that the light through the condensing lens 21 condensing light from a photographic subject enters and that has the three or more areas A formed by division in the direction around the optical axis Ox, and a picture selective-acquisition unit (the picture pickup element 3, the selector 41 and the control unit 7) that includes the picture pickup element 3 to form the pictures for the images that has passed through the pupil division unit 22 and that selectively acquires, by time division, the pickup pictures for the respective images that have passed through the different areas A in the pupil division unit 22.

Thereby, it is not necessary to individually provide a picture pickup optical system after the pupil division unit 22 and the picture pickup element 3 in each of the areas A, for individually picking up the images that have passed through the different areas A in the pupil division unit 22.

Therefore, it is possible to prevent an increase in apparatus size, in the case of properly presenting the respective stereoscopic pictures when the subject X is observed from the different angle directions.

The signification that the division number of the areas A is three or more will be described later.

Further, the pupil division unit 22 has the areas A the number of which is a multiple of two and four or more, and the stereoscopic picture generation apparatus 1 includes the picture addition units (42-1L to 42-4R) that add the plurality of pickup pictures acquired by the picture selective-acquisition unit, with the different combinations, respectively.

Thereby, for each of the angle directions whose number is a multiple of two and four or more, it is possible to obtain the left-eye picture by the addition between the pickup pictures for the images that have passed through the respective parts of the left-eye area of the observer at the position in the angle direction, and to obtain the right-eye picture by the addition between the pickup pictures for the images that have passed through the respective parts of the right-eye area.

Therefore, it is possible to support the observation from the angle directions whose number is a multiple of two and four or more.

Moreover, in the stereoscopic picture generation apparatus 1, the picture selective-acquisition unit acquires, by time division, the pickup pictures for the respective images that have passed through the different areas A in the pupil division unit 22, with the picture pickup element 3.

Thereby, when selectively acquiring the pickup pictures for the respective images that have passed through the different areas A, it is not necessary to simultaneously receive the respective images that have passed through the different areas, with the picture pickup element 3.

Therefore, in this case, the picture pickup element 3 does not have to be configured to receive the respective images that have passed through the different areas A, at different positions on the picture pickup surface, leading to a simple configuration and a cost reduction.

Furthermore, in the stereoscopic picture generation apparatus 1, the pupil division unit 22 can allow incident light to pass through the areas A/block incident light for each of the areas A, and the picture selective-acquisition unit sequentially selects the area A through which the incident light is to pass, and sequentially receives the image that has passed through the selected area A, with the picture pickup element 3.

Thereby, the pickup pictures for the respective images that have passed through the different areas A are selectively acquired by a simple technique of controlling the passing/blocking of incident light for each of the areas A. Therefore, it is possible to easily implement a stereoscopic picture generation apparatus that properly presents the respective stereoscopic pictures when a subject is observed from different angle directions.

In addition, the stereoscopic picture generation apparatus 1 includes the picture rotation processing units (the second rotation processing unit 44-2L to the fourth rotation processing unit 44-4R) that rotate the left-eye pictures GL and right-eye pictures GR obtained based on the pickup pictures acquired by the picture selective-acquisition unit.

Thereby, it is possible to match the orientation of the subject X exhibited on the stereoscopic picture that is actualized by the left-eye picture GL and the right-eye picture GR, with the orientation of the subject X when the observer actually observes the subject X from the angle direction of his position relative to the subject X. Therefore, it is possible to achieve the prevention of the occurrence of an uncomfortable feeling caused by a mismatch between the orientation of the subject X on the stereoscopic picture and the orientation of the subject X when the subject X is actually observed.

2. Second Embodiment 2-1. Configuration and Operation

FIG. 5 is a block diagram showing an internal configuration of a stereoscopic picture generation apparatus 1A according to a second embodiment.

Similarly to the stereoscopic picture generation apparatus 1 according to the first embodiment, the stereoscopic picture generation apparatus 1A according to the second embodiment selectively acquires, by time division, the pickup pictures for the respective images that have passed through the different areas A.

In the following explanation, as for the same parts as the previously explained parts, the same reference characters are assigned and the explanation is omitted.

Compared to the stereoscopic picture generation apparatus 1, the stereoscopic picture generation apparatus 1A is different in that an optical unit 2A is provided instead of the optical unit 2, a left-right picture individual-generation unit 4A is provided instead of the left-right picture individual-generation unit 4, a control unit 7A is provided instead of the control unit 7, and an illumination unit 8A is provided instead of the illumination unit 8.

The optical unit 2A is different from the optical unit 2 in that a pupil division unit 22A is provided instead of the pupil division unit 22.

The configuration of the pupil division unit 22A will be described later.

As shown in FIG. 6A, the illumination unit 8A includes a laser drive unit 81 and a plurality of LDs (laser diodes) 82. As the plurality of LDs 82, a first red-color LD 82R1, second red-color LD 82R2, third red-color LD 82R3 and fourth red-color LD 82R4 that emit the light with a red-color wavelength band, a first green-color LD 82G1, second green-color LD 82G2, third green-color LD 82G3 and fourth green-color LD 82G4 that emit the light with a green-color wavelength band, and, a first blue-color LD 82B 1, second blue-color LD 82B2, third blue-color LD 82B3 and fourth blue-color LD 82B4 that emit the light with a blue-color wavelength band are included. The first red-color LD 82R1, the second red-color LD 82R2, the third red-color LD 82R3 and the fourth red-color LD 82R4 can emit lights with different wavelength bands in the red-color wavelength band, respectively. Concretely, in the case where the respective wavelength bands when the red-color wavelength band is divided into four wavelength bands are wavelength bands R1, R2, R3 and R4 as shown in FIG. 6B, the first red-color LD 82R1 can emit the light with the wavelength band R1, the second red-color LD 82R2 can emit the light with the wavelength band R2, the third red-color LD 82R3 can emit the light with the wavelength band R3, and the fourth red-color LD 82R4 can emit the light with the wavelength band R4.

Also, the green-color LDs 82 and the blue-color LDs 82 can emit lights with different wavelength bands in the respective color wavelength bands. Concretely, as for the green-color LDs 82, in the case where the respective wavelength bands when the green-color wavelength band is divided into four wavelength bands are wavelength bands G1, G2, G3 and G4 as shown in FIG. 6B, the first green-color LD 82G1 can emit the light with the wavelength band G1, the second green-color LD 82G2 can emit the light with the wavelength band G2, the third green-color LD 82G3 can emit the light with the wavelength band G3, and the fourth green-color LD 82G4 can emit the light with the wavelength band G4. As for the blue-color LDs 82, in the case where the respective wavelength bands when the blue-color wavelength band is divided into four wavelength bands are wavelength bands B1, B2, B3 and B4 as shown in FIG. 6B, the first blue-color LD 82B 1 can emit the light with the wavelength band B1, the second blue-color LD 82B2 can emit the light with the wavelength band B2, the third blue-color LD 82B3 can emit the light with the wavelength band B3, and the fourth blue-color LD 82B4 can emit the light with the wavelength band B4.

The laser drive unit 81 drives the emission of an LD 82 designated by an instruction signal SL from the control unit 7A.

FIG. 7 is an explanatory diagram for a configuration of the pupil division unit 22A. In the figure, the pupil division unit 22A is viewed from the image surface side.

The pupil division unit 22A is divided such that the areas A1 to A4 are formed similarly to the pupil division unit 22. In the pupil division unit 22A, each of the areas A1 to A4 is configured by a wavelength filter. The area A1 is configured by a wavelength filter 22Aa, the area A2 is configured by a wavelength filter 22Ab, the area A3 is configured by a wavelength filter 22Ac, and the area A4 is configured by a wavelength filter 22Ad.

The wavelength filters 22Aa to 22Ad are configured as so-called multiband-pass filters, and selectively transmit lights with three wavelength bands. Concretely, the wavelength filter 22Aa transmits the lights with the wavelength bands R1, G1 and B1, and the wavelength filter 22Ab transmits the lights with the wavelength bands R2, G2 and B2. Further, the wavelength filter 22Ac transmits the lights with the wavelength bands R3, G3 and B3, and the wavelength filter 22Ad transmits the lights with the wavelength bands R4, G4 and B4.

Getting back to FIG. 5, the control unit 7A controls the ON/OFF of the LDs 82 in the illumination unit 8A by the instruction signal SL, as follows. That is, a set of the first red-color LD 82R1, the first green-color LD 82G1 and the first blue-color LD 82B 1, a set of the second red-color LD 82R2, the second green-color LD 82G2 and the second blue-color LD 82B2, a set of the third red-color LD 82R3, the third green-color LD 82G3 and the third blue-color LD 82B3, and a set of the fourth red-color LD 82R4, the fourth green-color LD 82G4 and the fourth blue-color LD 82B4 are turned on sequentially and alternately. The control unit 7A executes the control of sequentially turning on each set of the LDs 82 in this way, repeatedly in a predetermined cycle.

Thereby, the lights with the wavelength bands R1, G1 and B1, the lights with the wavelength bands R2, G2 and B2, the lights with the wavelength bands R3, G3 and B3, and the lights with the wavelength bands R4, G4 and B4 sequentially enter the pupil division unit 22A, as the light from the photographic subject.

In a period during which the lights with the wavelength bands R1, G1 and B1 enter the pupil division unit 22A, the lights pass through only the area A1. In a period during which the lights with the wavelength bands R2, G2 and B2 enter the pupil division unit 22A, the lights pass through only the area A2. In a period during which the lights with the wavelength bands R3, G3 and B3 enter the pupil division unit 22A, the lights pass through only the area A3. In a period during which the lights with the wavelength bands R4, G4 and B4 enter the pupil division unit 22A, the lights pass through only the area A4.

In this regard, also, in the stereoscopic picture generation apparatus 1A according to the second embodiment, the period t1 during which incident light passes through only the area A1, the period t2 during which incident light passes through only the area A2, the period t3 during which incident light passes through only the area A3, and the period t4 during which incident light passes through only the area A4 are repeated in a predetermined cycle.

Similarly to the control unit 7, the control unit 7A controls the picture pickup operation of the picture pickup element 3 such that the picture pickup element 3 individually acquires the pickup picture signal in each of the period t1 to the period t4. Thereby, similarly to the first embodiment, the pickup picture signal Ga1, the pickup picture signal Ga2, the pickup picture signal Ga3 and the pickup picture signal Ga4 are acquired individually in the time axis direction.

Here, as described above, also, in the second embodiment, the pickup picture signal Ga1, the pickup picture signal Ga2, the pickup picture signal Ga3 and the pickup picture signal Ga4 are acquired individually in the time axis direction, and therefore, if using the same left-right picture individual-generation unit 4 as the first embodiment, it is possible to present stereoscopic pictures corresponding to the respective angle directions of 0 deg, 90 deg, 180 deg and 270 deg. However, each of the pickup picture signal Ga1, pickup picture signal Ga2, pickup picture signal Ga3 and pickup picture signal Ga4 obtained in the second embodiment lacks color components of predetermined wavelength bands for each of the red-color wavelength band, green-color wavelength band and blue-color wavelength band. Concretely, the pickup picture signal Ga1 lacks the color components of the wavelength bands other than the wavelength bands R1, G1 and B1, and the pickup picture signal Ga2 lacks the color components of the wavelength bands other than the wavelength bands R2, G2 and B2. Further, the pickup picture signal Ga3 lacks the color components of the wavelength bands other than the wavelength bands R3, G3 and B3, and the pickup picture signal Ga4 lacks the color components of the wavelength bands other than the wavelength bands R4, G4 and B4.

In view of this, the stereoscopic picture generation apparatus 1A is provided with the left-right picture individual-generation unit 4A shown in FIG. 8, instead of the left-right picture individual-generation unit 4.

Compared to the left-right picture individual-generation unit 4, the left-right picture individual-generation unit 4A is different in that color compensation units 45 are interposed between the selector 41 and the addition units 42, respectively.

Concretely, a first left-side color compensation unit 45-1L is interposed between the output terminal TL1 of the selector 41 and the first left-side addition unit 42-1L, a first right-side color compensation unit 45-1R is interposed between the output terminal TR1 and the first right-side addition unit 42-1R, a second left-side color compensation unit 45-2L is interposed between the output terminal TL2 and the second left-side addition unit 42-2L, a second right-side color compensation unit 45-2R is interposed between the output terminal TR2 and the second right-side addition unit 42-2R, a third left-side color compensation unit 45-3L is interposed between the output terminal TL3 and the third left-side addition unit 42-3L, a third right-side color compensation unit 45-3R is interposed between the output terminal TR3 and the third right-side addition unit 42-3R, a fourth left-side color compensation unit 45-4L is interposed between the output terminal TL4 and the fourth left-side addition unit 42-4L, and a fourth right-side color compensation unit 45-4R is interposed between the output terminal TR4 and the fourth right-side addition unit 42-4R.

The control unit 7A performs the same control as the control unit 7, as the selection control of the output terminals T to the selector 41. That is, the type of the pickup picture signals Ga to be output from the respective terminals T of the terminals TL1 to TR4 in the respective periods t of the period t1 to the period t4 is the same as the first embodiment.

The relation between the first left-side color compensation unit 45-1L to the fourth right-side color compensation unit 45-4R and the color components of the pickup picture signals Ga to be input to them is shown for each period t, as follows.

45-1L
t1: Ga1 (R1, G1, B1), t2: Ga2 (R2, G2, B2)
45-1R
t3: Ga3 (R3, G3, B3), t4: Ga4 (R4, G4, B4)
45-2L
t2: Ga2 (R2, G2, B2), t3: Ga3 (R3, G3, B3)
45-2R
t1: Ga1 (R1, G1, B1), t4: Ga4 (R4, G4, B4)
45-3L
t3: Ga3 (R3, G3, B3), t4: Ga4 (R4, G4, B4)
45-3R
t1: Ga1 (R1, G1, B1), t2: Ga2 (R2, G2, B2)
45-4L
t1: Ga1 (R1, G1, B1), t4: Ga4 (R4, G4, B4)
45-4R
t2: Ga2 (R2, G2, B2), t3: Ga3 (R3, G3, B3)

The first left-side color compensation unit 45-1L and the third right-side color compensation unit 45-3R, to which only the pickup picture signal Ga1 and the pickup picture signal Ga2 are input, can selectively execute, for the input pickup picture signals Ga, a process to compensate the color components other than the wavelength bands R1, G1 and B1 (hereinafter, referred to as a "for-first-wavelength compensation process") and a process to compensate the color components other than the wavelength bands R2, G2 and B2 (referred to as a "for-second-wavelength compensation process"). The first right-side color compensation unit 45-1R and the third left-side color compensation unit 45-3L, to which only the pickup picture signal Ga3 and the pickup picture signal Ga4 are input, can selectively execute, for the input pickup picture signals Ga, a process to compensate the color components other than the wavelength bands R3, G3 and B3 (referred to as a "for-third-wavelength compensation process") and a process to compensate the color components other than the wavelength bands R4, G4 and B4 (referred to as a "for-fourth-wavelength compensation process"). Further, the second left-side color compensation unit 45-2L and the fourth right-side color compensation unit 45-4R, to which only the pickup picture signal Ga2 and the pickup picture signal Ga3 are input, can selectively execute, for the input pickup picture signals Ga, the for-second-wavelength compensation process and the for-third-wavelength compensation process, and the second right-side color compensation unit 45-2R and the fourth left-side color compensation unit 45-4L, to which only the pickup picture signal Ga1 and the pickup picture signal Ga4 are input, can selectively execute, for the input pickup picture signals Ga, the for-first-wavelength compensation process and the for-fourth-wavelength compensation process.

To the first left-side color compensation unit 45-1L to the fourth right-side color compensation unit 45-4R, the control unit 7A performs such a control that the following compensation processes are executed on a period t basis.

t1
To 45-1L, 45-2R, 45-3R and 45-4L, for-first-wavelength compensation process t2
To 45-1L, 45-2L, 45-3R and 45-4R, for-second-wavelength compensation process t3
To 45-1R, 45-2L, 45-3L and 45-4R, for-third-wavelength compensation process t4
To 45-1R, 45-2R, 45-3L and 45-4L, for-fourth-wavelength compensation process Thereby, it is possible to properly compensate the color components lacked by passage through the pupil division unit 22A, and to properly present the stereoscopic picture as a color picture.

2-2. Summary of Second Embodiment

As described above, the stereoscopic picture generation apparatus 1A according to the second embodiment includes the pupil division unit 22A that the light through the condensing lens 21 condensing light from the photographic subject enters and that has the three or more areas A formed by division in the direction around the optical axis Ox, and a picture selective-acquisition unit (the illumination unit 8A, the picture pickup element 3, the selector 41 and the control unit 7A) that includes the picture pickup element 3 to form the pictures for the images that have passed through the pupil division unit 22A and that selectively acquires, by time division, the pickup pictures for the respective images that have passed through the different areas A in the pupil division unit 22A.

Thereby, similarly to the first embodiment, it is not necessary to individually provide a picture pickup optical system after the pupil division unit 22A and the picture pickup element 3 in each of the areas A, for individually picking up the images that have passed through the different areas A in the pupil division unit 22A.

Therefore, it is possible to prevent an increase in apparatus size, in the case of properly presenting the respective stereoscopic pictures when the subject X is observed from the different angle directions.

Further, similarly to the first embodiment, in the stereoscopic picture generation apparatus 1A, the picture selective-acquisition unit acquires, by time division, the pickup pictures for the respective images that have passed through the different areas A in the pupil division unit 22A, with the picture pickup element 3.

This leads to a simple configuration of the picture pickup element 3 and a cost reduction, similarly to the first embodiment.

Moreover, in the stereoscopic picture generation apparatus 1A, the pupil division unit 22A is configured such that, through the areas A, the lights with the different wavelength bands selectively pass, each of which has the respective wavelength bands of the red-color wavelength band, the green-color wavelength band and the blue-color wavelength band. The picture pickup element 3 can receive the lights with the red-color wavelength band, the green-color wavelength band and the blue-color wavelength band. The picture selective-acquisition unit includes the variable wavelength illumination unit (illumination unit 8A) that can selectively emit, as illumination light to the photographic subject, the lights with the same wavelength bands respectively as the lights with the wavelength bands to pass through the individual areas A in the pupil division unit 22A, and sequentially emits the lights with the different wavelength bands, with the variable wavelength illumination unit, while sequentially receiving the lights that have passed through the pupil division unit 22A for each switching of the emission wavelengths of the variable wavelength illumination unit, with the picture pickup element 3.

Thereby, the pickup pictures for the respective images that have passed through the different areas A are selectively acquired by the simple technique of switching the emission wavelengths of the variable wavelength illumination unit.

Therefore, it is possible to easily implement a stereoscopic picture generation apparatus that properly presents the respective stereoscopic pictures when a subject is observed from different angle directions.

3. Third Embodiment

3-1. Configuration and Operation

FIG. 9 is a block diagram showing an internal configuration of a stereoscopic picture generation apparatus 1B according to a third embodiment.

The stereoscopic picture generation apparatus 1B according to the third embodiment selectively acquires the pickup pictures for the respective images that have passed through the different areas A, by utilizing the difference in wavelength of the respective images.

Compared to the stereoscopic picture generation apparatus 1A according to the second embodiment, the stereoscopic picture generation apparatus 1B is different in that a picture pickup element 3A is provided instead of the picture pickup element 3, a left-right picture individual-generation unit 4B is provided instead of the left-right picture individual-generation unit 4A, a control unit 7B is provided instead of the control unit 7A, and an illumination unit 8 is provided instead of the illumination unit 8A.

The control unit 7B controls the picture pickup element 3A such that it sequentially acquires pickup picture signals in a predetermined cycle.

Similarly to the first embodiment, the illumination unit 8 illuminates the photographic subject, which is the subject X, by white light.

FIG. 10 is an explanatory diagram for a configuration of the picture pickup element 3A, and shows a part of the picture pickup surface side of the picture pickup element 3A in an enlarged manner.

Similarly to the picture pickup element 3, the picture pickup element 3A is an RGGB-type picture pickup element.

Here, in the RGGB-type picture pickup element, four pixels of horizontally two pixels and vertically two pixels constitute one RGGB unit. In the RGGB unit, color filters (wavelength filters) to selectively transmit the lights with the red wavelength band, the green wavelength band and the blue wavelength band are formed on the upper-left pixel, the upper-right and lower-left pixels and the lower-right pixel, respectively. That is, the upper-left pixel is a red-color pixel, the upper-right and lower-left pixels are green-color pixels, and the lower-right pixel is a blue-color pixel.

In a typical RGGB-type picture pickup element (picture pickup element 3), the RGGB units are arrayed horizontally and vertically. However, the picture pickup element 3A includes, as the RGGB unit, four types of RGGB units U1, U2, U3 and U4 that are configured to differ in the transmission wavelength band for each of the red-color wavelength band, green-color wavelength band and blue-color wavelength band. Then, blocks B each of which is constituted by these RGGB units U1 to U4 and includes sixteen pixels of horizontally four pixels and vertically four pixels are arrayed horizontally and vertically.

As shown in the figure, the RGGB unit U1 is constituted by a pixel that is a red-color pixel and on which a wavelength filter to selectively transmit the light with the wavelength band R1 is formed, a pixel that is a green-color pixel and on which a wavelength filter to selectively transmit the light with the wavelength band G1 is formed, and a pixel that is a blue-color pixel and on which a wavelength filter to selectively transmit the light with the wavelength band B1 is formed. The RGGB unit U2 is constituted by a pixel that is a red-color pixel and on which a wavelength filter to selectively transmit the light with the wavelength band R2 is formed, a pixel that is a green-color pixel and on which a wavelength filter to selectively transmit the light with the wavelength band G2 is formed, and a pixel that is a blue-color pixel and on which a wavelength filter to selectively transmit the light with the wavelength band B2 is formed. The RGGB unit U3 is constituted by a pixel that is a red-color pixel and on which a wavelength filter to selectively transmit the light with the wavelength band R3 is formed, a pixel that is a green-color pixel and on which a wavelength filter to selectively transmit the light with the wavelength band G3 is formed, and a pixel that is a blue-color pixel and on which a wavelength filter to selectively transmit the light with the wavelength band B3 is formed. The RGGB unit U4 is constituted by a pixel that is a red-color pixel and on which a wavelength filter to selectively transmit the light with the wavelength band R4 is formed, a pixel that is a green-color pixel and on which a wavelength filter to selectively transmit the light with the wavelength band G4 is formed, and a pixel that is a blue-color pixel and on which a wavelength filter to selectively transmit the light with the wavelength band B4 is formed. The arrangement position relation of the RGGB units U1 to U4 in each block B is common. In the embodiment, the RGGB unit U1 is positioned at the upper left, the RGGB unit U2 is positioned at the upper right, the RGGB unit U3 is positioned at the lower left, and the RGGB unit U4 is positioned at the lower right, in each block B.

According to the picture pickup element 3A configured in the above described way, the image that has passed through the area A1 in the pupil division unit 22A is picked up (light-received) by only the RGGB unit U1, and the image that has passed through the area A2 is picked up by only the RGGB unit U2. Further, the image that has passed through the area A3 is picked up by only the RGGB unit U3, and the image that has passed through the area A4 is picked up by only the RGGB unit U4.

FIG. 11 is an explanatory diagram for an internal configuration of the left-right picture individual-generation unit 4B.

The left-right picture individual-generation unit 4B is different in the configuration of the former stage of the first left-side addition unit 42-1L to the fourth right-side addition unit 42-4R, compared to the left-right picture individual-generation unit 4A, and the configuration of the other part is the same as the left-right picture individual-generation unit 4A.

In the left-right picture individual-generation unit 4B, the pickup picture signals obtained by the picture pickup element 3A are input to a first area-passing-image extraction unit 46-1, a second area-passing-image extraction unit 46-2, a third area-passing-image extraction unit 46-3 and a fourth area-passing-image extraction unit 46-4, respectively.

Each area-passing-image extraction unit 46 extracts the pixel values at previously determined pixel positions, from the pickup picture based on the pickup picture signal input by the picture pickup element 3A.

FIG. 12A to FIG. 12D show the respective pixel positions for which the first area-passing-image extraction unit 46-1 to the fourth area-passing-image extraction unit 46-4 perform the extraction, by voids.

The first area-passing-image extraction unit 46-1 extracts the pixel values at the same pixel positions as the RGGB unit U1 (FIG. 12A). Further, the second area-passing-image extraction unit 46-2 extracts the pixel values at the same pixel positions as the RGGB unit U2 (FIG. 12B), the third area-passing-image extraction unit 46-3 extracts the pixel values at the same pixel positions as the RGGB unit U3 (FIG. 12C), and the fourth area-passing-image extraction unit 46-4 extracts the pixel values at the same pixel positions as the RGGB unit U4 (FIG. 12D).

The "extraction" mentioned here means that the pixel values at the pixel positions other than the intended pixel positions are eliminated from the original pickup picture (for example, "0" is set).

The pickup picture after the extraction process by the first area-passing-image extraction unit 46-1 is input to a first interpolation processing unit 47-1, the pickup picture after the extraction process by the second area-passing-image extraction unit 46-2 is input to a second interpolation processing unit 47-2, the pickup picture after the extraction process by the third area-passing-image extraction unit 46-3 is input to a third interpolation processing unit 47-3, and the pickup picture after the extraction process by the fourth area-passing-image extraction unit 46-4 is input to a fourth interpolation processing unit 47-4.

For the input pickup picture, each interpolation processing unit 47 interpolates the pixel values at the pixel positions other than the pixel positions for which the pixel values have been extracted.

Concretely, the first interpolation processing unit 47-1 interpolates the pixel values at the pixel positions other than the same pixel positions as the RGGB unit U1 based on the pixel values at the same pixel positions as the RGGB unit U1. Further, the second interpolation processing unit 47-2 interpolates the pixel values at the pixel positions other than the same pixel positions as the RGGB unit U2 based on the pixel values at the same pixel positions as the RGGB unit U2, the third interpolation processing unit 47-3 interpolates the pixel values at the pixel positions other than the same pixel positions as the RGGB unit U3 based on the pixel values at the same pixel positions as the RGGB unit U3, and the fourth interpolation processing unit 47-4 interpolates the pixel values at the pixel positions other than the same pixel positions as the RGGB unit U4 based on the pixel values at the same pixel positions as the RGGB unit U4.

The pickup picture after the interpolation process by the first interpolation processing unit 47-1 is input to a first color compensation unit 48-1, the pickup picture after the interpolation process by the second interpolation processing unit 47-2 is input to a second color compensation unit 48-2, the pickup picture after the interpolation process by the third interpolation processing unit 47-3 is input to a third color compensation unit 48-3, and the pickup picture after the interpolation process by the fourth interpolation processing unit 47-4 is input to a fourth color compensation unit 48-4.

Each color compensation unit 48 executes a process to compensate lacked color components, for the input pickup picture.

Here, the pickup picture after the extraction process by the first area-passing-image extraction unit 46-1 corresponds to the pickup picture for the image that has passed through the area A1, and therefore, lacks the color components other than the wavelength bands R1, G1 and B1. The pickup picture after the extraction process by the second area-passing-image extraction unit 46-2 corresponds to the pickup picture for the image that has passed through the area A2, and therefore, lacks the color components other than the wavelength bands R2, G2 and B2. The pickup picture after the extraction process by the third area-passing-image extraction unit 46-3 corresponds to the pickup picture for the image that has passed through the area A3, and therefore, lacks the color components other than the wavelength bands R3, G3 and B3. The pickup picture after the extraction process by the fourth area-passing-image extraction unit 46-4 corresponds to the pickup picture for the image that has passed through the area A4, and therefore, lacks the color components other than the wavelength bands R4, G4 and B4.

The first color compensation unit 48-1 executes the above described for-first-wavelength compensation process for the input pickup picture. Further, the second color compensation unit 48-2 executes the above described for-second-wavelength compensation process for the input pickup picture, the third color compensation unit 48-3 executes the above described for-third-wavelength compensation process for the input pickup picture, and the fourth color compensation unit 48-4 executes the above described for-fourth-wavelength compensation process for the input pickup picture.

Thereby, it is possible to properly compensate the color components lacked by passage through the pupil division unit 22A.

In this case, to each of the first left-side addition unit 42-1L to the fourth right-side addition unit 42-4R, the pickup pictures are input from the two corresponding color compensation units 48 of the first color compensation unit 48-1 to the fourth color compensation unit 48-4. The connection relation between the first left-side addition unit 42-1L to the fourth right-side addition unit 42-4R and the first color compensation unit 48-1 to the fourth color compensation unit 48-4 is as follows.

42-1L . . . 48-1 and 48-2
42-1R . . . 48-3 and 48-4
42-2L . . . 48-2 and 48-3
42-2R . . . 48-1 and 48-4
42-3L . . . 48-3 and 48-4
42-3R . . . 48-1 and 48-2
42-4L . . . 48-1 and 48-4
42-4R . . . 48-2 and 48-3

Thereby, the pickup pictures are properly added, for each of the left-eye areas and right-eye areas of the respective observers at the positions in the angle directions of 0 deg, 90 deg, 180 deg and 270 deg.

3-2. Summary of Third Embodiment

As described above, the stereoscopic picture generation apparatus 1B according to the third embodiment includes the pupil division unit 22A that the light through the condensing lens 21 condensing light from the photographic subject enters and that has the three or more areas A formed by division in the direction around the optical axis Ox, and a picture selective-acquisition unit (the picture pickup element 3A, and the first area-passing-image extraction unit 46-1 to the fourth area-passing-image extraction unit 46-4) that includes the picture pickup element 3A to form the pictures for the images that have passed through the pupil division unit 22A and that selectively acquires the pickup pictures for the respective images that have passed through the different areas A in the pupil division unit 22A, by utilizing the difference in wavelength of the respective images.

Thereby, it is not necessary to individually provide a picture pickup optical system after the pupil division unit 22A and the picture pickup element 3A in each of the areas A, for individually picking up the images that have passed through the different areas A in the pupil division unit 22A.

Therefore, it is possible to prevent an increase in apparatus size, in the case of properly presenting the respective stereoscopic pictures when the subject X is observed from the different angle directions.

In the stereoscopic picture generation apparatus 1B, the pupil division unit 22A is configured such that the lights with the different wavelength bands selectively pass through the areas A and the picture pickup element 3A arranges, at the different positions on the picture pickup surface, the plurality of the wavelength filters to selectively transmit the lights with the same wavelength bands as the lights that have passed through the different areas A in the pupil division unit 22A, respectively.

Thereby, the images that have passed through the areas A are individually picked up at the different positions on the picture pickup surface, respectively.

Therefore, it is possible to simultaneously acquire the pickup pictures for the images that have passed through the respective areas A.

Here, the display period for a single piece of stereoscopic picture, that is, the display period for a single piece of left-eye picture GL and a single piece of right-eye picture GR is referred to as the "single-display period". As described above, the pickup pictures for the images that have passed through the respective areas A can be simultaneously acquired, and therefore, unlike the first and second embodiments, it is not necessary to separate the single-display period into the plurality of periods t. Thereby, it is possible to slow the shutter speed of the picture pickup element 3A, resulting in an advantage when picking up a picture for a dark photographic subject or a fast-moving photographic subject.

Further, since the pickup pictures for the images that have passsed through the respective areas A can be simultaneously acquired as described above, the number of picture pickups by the picture pickup element 3A necessary for presenting a single piece of stereoscopic picture is "1". Therefore, the number of picture pickups by the picture pickup element 3A can be decreased compared to the case of the time division acquisition as the first and second embodiments.

Moreover, in the stereoscopic picture generation apparatus 1B, the pupil division unit 22A is configured such that, through the areas A, the lights with the different wavelength bands selectively pass, each of which has the respective wavelength bands of the red-color wavelength band, the green-color wavelength band and the blue-color wavelength band, and the picture pickup element 3A arranges, at the different positions on the picture pickup surface, the plurality of the wavelength filters to selectively transmit the lights with the same wavelength bands as the lights that have passed through the different areas A in the pupil division unit 22A, respectively.

Thereby, the pickup pictures for the images that have passed through the areas A are individually picked up at the different positions on the picture pickup surface, respectively, and therewith, color pictures are obtained as the pickup pictures. Therefore, it is possible to present stereoscopic pictures that have a high visibility due to the color pictures.

4. Fourth Embodiment

4-1. Configuration and Operation

FIG. 13 is a block diagram showing an internal configuration of a stereoscopic picture generation apparatus 1C according to a fourth embodiment.

The stereoscopic picture generation apparatus 1C according to the fourth embodiment selectively acquires the pickup pictures for the respective images that have passed through the different areas A, by utilizing the difference in wavelength and polarization of the respective images.

Compared to the stereoscopic picture generation apparatus 1B according to the third embodiment, the stereoscopic picture generation apparatus 1C is different in that an optical unit 2B is provided instead of the optical unit 2A, a picture pickup element 3B is provided instead of the picture pickup element 3A, and a left-right picture individual-generation unit 4C is provided instead of the left-right picture individual-generation unit 4B.

Compared to the optical unit 2A, the optical unit 2B is different in that a pupil division unit 22B is provided instead of the pupil division unit 22A. The pupil division unit 22B includes a wavelength separation element 24 and a polarization separation element 25. These wavelength separation element 24 and polarization separation element 25 are arranged so as to be overlapped in the optical axis direction. In the embodiment, these wavelength separation element 24 and polarization separation element 25 are bonded so as to be faced. In the pupil division unit 22B according to the embodiment, the wavelength separation element 24 and the polarization separation element 25 are arranged, in that order, from the photographic subject side to the image surface side, but, the arrangement relation may be reversed.

FIG. 14A is an explanatory diagram for a configuration of the wavelength separation element 24.

The wavelength separation element 24 includes a wavelength filter 24a that selectively transmits the lights with the wavelength bands R1, G1 and B1, and a wavelength filter 24b that selectively transmits the lights with the wavelength bands R2, G2 and B2. The wavelength separation element 24 has two areas partitioned by a single dividing line intersecting with the optical axis Ox. The wavelength filter 24a is formed in one area, and the wavelength filter 24b is formed in the other area.

In the embodiment, the dividing line partitioning between the wavelength filter 24a and the wavelength filter 24b is parallel to the 90 deg-270 deg axis. Across this dividing line, the wavelength filter 24a is formed on the 0 deg side, and the wavelength filter 24b is formed on the 180 deg side.

FIG. 14B is an explanatory diagram for a configuration of the polarization separation element 25.

The polarization separation element 25 includes a polarizing plate 25a and a polarizing plate 25b. The polarization separation element 25 has two areas partitioned by a single dividing line intersecting with the optical axis Ox. The polarizing plate 25a is formed in one area, and the polarizing plate 25b is formed in the other area.

In the embodiment, the dividing line partitioning between the polarizing plate 25a and the polarizing plate 25b is parallel to the 0 deg-180 deg axis. Across this dividing line, the polarizing plate 25a is formed on the 90 deg side, and the polarizing plate 25b is formed on the 270 deg side.

As shown by the solid-line arrow in the figure, the transmission axis of the polarizing plate 25a is parallel to the 90 deg-270 deg axis. That is, the polarizing plate 25a selectively transmits a linearly-polarized light that is in the polarization direction parallel to the 90 deg-270 deg axis. On the other hand, the transmission axis of the polarizing plate 25b is parallel to the 0 deg-180 deg axis, and the polarizing plate 25b selectively transmits a linearly-polarized light that is in the polarization direction parallel to the 0 deg-180 deg axis.

Hereinafter, the polarization direction parallel to the 90 deg-270 deg axis is referred to as the "first polarization direction", and the polarization direction parallel to the 0 deg-180 deg axis is referred to as the "second polarization direction".

Since the wavelength separation element 24 and the polarization separation element 25 are arranged so as to be overlapped in the optical axis direction, the pupil division unit 22B is divided into four areas A, by each dividing line of the wavelength separation element 24 and the polarization separation element 25. Here, similarly to the first and second embodiments, in the four areas A, an area A of 0 deg to 90 deg is referred to as an "area A1", an area A of 90 deg to 180 deg is referred to as an "area A2", an area A of 180 deg to 270 deg is referred to as an "area A3", and an area A of 270 deg to 0 deg (360 deg) is referred to as an "area A4".

In the pupil division unit 22B, the area A1 is an area A that transmits the light by the combination of the wavelength bands R1, G1 and B1 and the first polarization direction, as the combination of the wavelength band and the polarization. The area A2 is an area A that transmits the light by the combination of the wavelength bands R2, G2 and B2 and the first polarization direction, the area A3 is an area A that transmits the light by the combination of the wavelength bands R2, G2 and B2 and the second polarization direction, and the area A4 is an area A that transmits the light by the combination of the wavelength bands R1, G1 and B1 and the second polarization direction.

FIG. 15 is an explanatory diagram for a configuration of the picture pickup element 3B. In this figure, the horizontal pixel number is represented by n, and the vertical pixel number is represented by m.

The picture pickup element 3B includes a plurality of wavelength filters (image-surface-side wavelength filters) that selectively transmit the lights with the same wavelength bands as the lights that have passed through the wavelength filters 24a and 24b, respectively, and polarizing plates 3Ba and 3Bb (image-surface-side polarizing plates) that selectively transmit the polarized lights in the same polarization direction as the polarized lights that have passed through the polarizing plates 25a and 25b, respectively.

In the picture pickup element 3B, as vertically extending columns, a column in which only the RGGB units U1 are arrayed, and a column in which only the RGGB units U2 are arrayed, are arrayed horizontally and alternately. Then, the polarizing plate 3Ba that selectively transmits the polarized light in the first polarization direction, and the polarizing plate 3Bb that selectively transmits the polarized light in the second polarization direction are arranged alternately on a two-horizontal-line basis. Each of the polarizing plate 3Ba and the polarizing plate 3Bb is formed so as to cover the respective wavelength filters formed on the RGGB units U1 and U2. That is, the polarizing plate 3Ba and the polarizing plate 3Bb are arranged so as to be overlapped with these wavelength filters, in the optical axis direction.

By such a configuration, in the picture pickup element 3B, the respective types of wavelength filters formed on the RGGB units U1 and U2, and the polarizing plates 3Ba and 3Bb are arranged in different combination at different positions on the surface parallel to the picture pickup surface, respectively, so as to be overlapped in the optical axis direction.

Concretely, in the configuration of the picture pickup element 3B shown in FIG. 15, on the picture pickup surface, there are four types of parts: a part in which the polarizing plate 3Ba is overlapped with the RGGB unit U1, a part in which the polarizing plate 3Ba is overlapped with the RGGB unit U2, a part in which the polarizing plate 3Bb is overlapped with the RGGB unit U2, and a part in which the polarizing plate 3Bb is overlapped with the RGGB unit U1. These parts are, in the same order, a part through which the light by the same combination of the wavelength and the polarization as the light that has passed through the area A1 passes, a part through which the light by the same combination of the wavelength and the polarization as the light that has passed through the area A2 passes, a part through which the light by the same combination of the wavelength and the polarization as the light that has passed through the area A3 passes, and a part through which the light by the same combination of the wavelength and the polarization as the light that has passed through the area A4 passes.

Thereby, in the picture pickup element 3B, the images that have passed through the areas A in the pupil division unit 22B are individually picked up at the different positions on the picture pickup surface, respectively.

FIG. 16 is an explanatory diagram for an internal configuration of the left-right picture individual-generation unit 4C.

The left-right picture individual-generation unit 4C is different in the configuration of the former stage of the first left-side addition unit 42-1L to the fourth right-side addition unit 42-4R, compared to the left-right picture individual-generation unit 4B. The configuration of the other part is the same as the left-right picture individual-generation unit 4B.

In the left-right picture individual-generation unit 4C, the pickup picture signals obtained by the picture pickup element 3B are input to a first area-passing-image extraction unit 46'-1, a second area-passing-image extraction unit 46'-2, a third area-passing-image extraction unit 46'-3, and a fourth area-passing-image extraction unit 46'-4.

Each area-passing-image extraction unit 46' extracts the pixel values at previously determined pixel positions, from the pickup picture based on the pickup picture signal input by the picture pickup element 3B.

FIG. 17A to FIG. 17D show the respective pixel positions for which the first area-passing-image extraction unit 46'-1 to the fourth area-passing-image extraction unit 46'-4 perform the extraction, by voids.

The first area-passing-image extraction unit 46'-1 extracts the pixel values at the same pixel positions as the RGGB unit U1 with which the polarizing plate 3Ba is overlapped (FIG. 17A). The second area-passing-image extraction unit 46'-2 extracts the pixel values at the same pixel positions as the RGGB unit U2 with which the polarizing plate 3Ba is overlapped (FIG. 17B), the third area-passing-image extraction unit 46'-3 extracts the pixel values at the same pixel positions as the RGGB unit U2 with which the polarizing plate 3Bb is overlapped (FIG. 17C), and the fourth area-passing-image extraction unit 46'-4 extracts the pixel values at the same pixel positions as the RGGB unit U1 with which the polarizing plate 3Bb is overlapped (FIG. 17D).

The pickup picture after the extraction process by the first area-passing-image extraction unit 46'-1 is input to a first interpolation processing unit 47'-1, the pickup picture after the extraction process by the second area-passing-image extraction unit 46'-2 is input to a second interpolation processing unit 47'-2, the pickup picture after the extraction process by the third area-passing-image extraction unit 46'-3 is input to a third interpolation processing unit 47'-3, and the pickup picture after the extraction process by the fourth area-passing-image extraction unit 46'-4 is input to a fourth interpolation processing unit 47'-4.

For the input pickup picture, each interpolation processing unit 47' interpolates the pixel values at the pixel positions other than the pixel positions for which the pixel values have been extracted. That is, the first interpolation processing unit 47'-1 interpolates the pixel values at the pixel positions other than the same pixel positions as the RGGB unit U1 with which the polarizing plate 3Ba is overlapped, based on the pixel values at the same pixel positions as the RGGB unit U1. The second interpolation processing unit 47'-2 interpolates the pixel values at the pixel positions other than the same pixel positions as the RGGB unit U2 with which the polarizing plate 3Ba is overlapped, based on the pixel values at the same pixel positions as the RGGB unit U2. The third interpolation processing unit 47'-3 interpolates the pixel values at the pixel positions other than the same pixel positions as the RGGB unit U2 with which the polarizing plate 3Bb is overlapped, based on the pixel values at the same pixel positions as the RGGB unit U2. The fourth interpolation processing unit 47'-4 interpolates the pixel values at the pixel positions other than the same pixel positions as the RGGB unit U1 with which the polarizing plate 3Bb is overlapped, based on the pixel values at the same pixel positions as the RGGB unit U1.

The left-right picture individual-generation unit 4C is provided with only two types of color compensation units 48: a first color compensation unit 48-1 corresponding to the RGGB unit U1 and a second color compensation unit 48-2 corresponding to the RGGB unit U2.

The pickup picture after the interpolation process by the first interpolation processing unit 47'-1 is input to one first color compensation unit 48-1, the pickup picture after the interpolation process by the second interpolation processing unit 47'-2 is input to one second color compensation unit 48-2, the pickup picture after the interpolation process by the third interpolation processing unit 47'-3 is input to the other second color compensation unit 48-2, and the pickup picture after the interpolation process by the fourth interpolation processing unit 47'-4 is input to the other first color compensation unit 48-1.

Thereby, the one first color compensation unit 48-1 compensates the color components lacked by passage through the area A1, and the one second color compensation unit 48-2 compensates the color components lacked by passage through the area A2. The other second color compensation unit 48-2 compensates the color components lacked by passage through the area A3, and the other first color compensation unit 48-1 compensates the color components lacked by passage through the area A4.

In this case, to each of the first left-side addition unit 42-1L to the fourth right-side addition unit 42-4R, the pickup pictures are input from the two corresponding color compensation units 48 of the four color compensation units 48, which includes the above two first color compensation units 48-1 and two second color compensation units 48-2. Concretely, the pickup pictures are input in accordance with the following correspondence relation.

42-1L . . . the one 48-1 and the one 48-2
42-1R . . . the other 48-2 and the other 48-1
42-2L . . . the one 48-2 and the other 48-2
42-2R . . . the one 48-1 and the other 48-1
42-3L . . . the other 48-2 and the other 48-1
42-3R . . . the one 48-1 and the one 48-2
42-4L . . . the one 48-1 and the other 48-1
42-4R . . . the one 48-2 and the other 48-2

4-2. Summary of Fourth Embodiment

As described above, the stereoscopic picture generation apparatus 1C according to the fourth embodiment includes the pupil division unit 22B that the light through the condensing lens 21 condensing light from the photographic subject enters and that has the three or more areas A formed by division in the direction around the optical axis Ox, and a picture selective-acquisition unit (the picture pickup element 3B, and the first area-passing-image extraction unit 46'-1 to the fourth area-passing-image extraction unit 46'-4) that includes the picture pickup element 3B to form the pictures for the images that have passed through the pupil division unit 22B and that selectively acquires the pickup pictures for the respective images that have passed through the different areas A in the pupil division unit 22B, by utilizing the difference in wavelength and polarization of the respective images.

Thereby, it is not necessary to individually provide a picture pickup optical system after the pupil division unit 22B and the picture pickup element 3B in each of the areas, for individually picking up the images that have passed through the different areas A in the pupil division unit 22B.

Therefore, it is possible to prevent an increase in apparatus size, in the case of properly presenting the respective stereoscopic pictures when the subject X is observed from the different angle directions.

Further, the area A is divided by utilizing difference in polarization as well as wavelength, and thereby, the type of wavelengths to be used is reduced. Here, many types of separation wavelengths make the production of wavelength filters difficult. In this regard, by the stereoscopic picture generation apparatus 1C according to the fourth embodiment, which reduces the type of wavelength to be used, it is possible to improve the ease of production of the wavelength filters to be used in the pupil division unit 22B.

Further, in the stereoscopic picture generation apparatus 1C, the pupil division unit 22B includes the wavelength separation element 24 that forms thereon the plurality of pupil-side wavelength filters (24a, 24b) to selectively transmit lights with different wavelength bands respectively, each of which has the respective wavelength bands of the red-color wavelength band, the green-color wavelength band and the blue-color wavelength band, and the polarization separation element 25 that forms thereon the plurality of pupil-side polarizing plates (25a, 25b) to selectively transmit the different polarized lights respectively. The wavelength separation element 24 and the polarization separation element 25 are arranged so as to be overlapped in the optical axis direction, and selectively transmit the lights with the different combinations of the wavelength bands and the polarizations for each of the areas A. Then, the picture pickup element 3B includes the plurality of the image-surface-side wavelength filters (the wavelength filters formed on the RGGB units U1 and U2 respectively) to selectively transmit the lights with the same wavelength bands as the lights that have passed through the different pupil-side wavelength filters respectively, and the plurality of the image-surface-side polarizing plates (3Ba, 3Bb) to selectively transmit the polarized lights in the same polarization directions as the polarized lights that have passed through the different pupil-side polarizing plates respectively. The image-surface-side wavelength filters and the image-surface-side polarizing plates are arranged with the different combinations at the different positions on the surface parallel to the picture pickup surface, respectively, so as to be overlapped in the optical axis direction.

Thereby, the images that have passed through the areas A are individually picked up at the different positions on the picture pickup surface, respectively. Further, as the pickup pictures for the images that have passed through the respective areas A, color pictures are obtained.

Thereby, it is possible to simultaneously acquire the pickup pictures for the images that have passed through the respective areas A, and to provide stereoscopic pictures that have a high visibility due to the color pictures.

5. Fifth Embodiment

5-1. Configuration and Operation

FIG. 18 is a block diagram showing an internal configuration of a stereoscopic picture generation apparatus 1D according to a fifth embodiment.

In the fifth embodiment, unlike the previous embodiments, the angle direction of the position of each observer is not fixed, and the movement of the observer is allowable. In the stereoscopic picture generation apparatus 1D, the third display unit 6-3 and the fourth display unit 6-4 are omitted, and only the first display unit 6-1 and the second display unit 6-2 are provided. These first display unit 6-1 and second display unit 6-2 are attached in a rotatable manner in the stereoscopic picture generation apparatus 1D, such that the angle direction in which the display surface is oriented can be changed. Concretely, in the embodiment, the first display unit 6-1 and the second display unit 6-2 are attached so as to be rotatable around a mirror body in which an optical unit 2' described later is incorporated.

Compared to the stereoscopic picture generation apparatus 1 according to the first embodiment, the stereoscopic picture generation apparatus 1D is different in that the optical unit 2' is provided instead of the optical unit 2, a left-right picture individual-generation unit 4D is provided instead of the left-right picture individual-generation unit 4, and a control unit 7C is provided instead of the control unit 7, and further, is different in that the third display control unit 5-3 and the fourth display control unit 5-4 are omitted in connection with the omission of the third display unit 6-3 and the fourth display unit 6-4, and in that a memory 9 is added.

The optical unit 2' is provided with a pupil division unit 22', instead of the pupil division unit 22 in the optical unit 2.

The memory 9 is a readable memory for the control unit 7C, and stores a control table 9a. The control table 9a will be described later.

FIG. 19A is an explanatory diagram for a configuration of the pupil division unit 22'.

The pupil division unit 22', in which a plurality of areas A are formed by division in the direction around the optical axis Ox, can allow incident light to pass through the areas A/block incident light for each of the areas A, similarly to the pupil division unit 22, but is different in that the division number of the areas A is "8". Concretely, the pupil division unit 22' is divided, by four dividing lines that intersect with the optical axis Ox, so that eight areas A are formed.

In this case, the dividing lines are parallel to the 0 deg-180 deg axis, the 45 deg-225 deg axis, the 90 deg-270 deg axis, and the 135 deg-315 deg axis, respectively, so that the eight area A are even areas. In the embodiment, of the eight areas A, an area A of 0 deg to 45 deg is referred to as an "area A1", an area A of 45 deg to 90 deg is referred to as an "area A2", an area A of 90 deg to 135 deg is referred to as an "area A3", an area A of 135 deg to 180 deg is referred to as an "area A4", an area A of 180 deg to 225 deg is referred to as an "area A5", an area A of 225 deg to 270 deg is referred to as an "area A6", an area A of 270 deg to 315 deg is referred to as an "area A7", and an area A of 315 deg to 0 deg is referred to as an "area A8".

Further, electronic shutters formed on the areas A1 to A8 are referred to as a "first electronic shutter 22'a", a "second electronic shutter 22'b", a "third electronic shutter 22'c", a "fourth electronic shutter 22'd", a "fifth electronic shutter 22'e", a "sixth electronic shutter 22'f", a "seventh electronic shutter 22'g" and an "eighth electronic shutter 22'h", respectively.

The opening/closing control of the first electronic shutter 22'a to the eighth electronic shutter 22'h in the pupil division unit 22' is performed by the control unit 7C.

FIG. 19B is an explanatory diagram for the movable range of the observer.

The solid-line arrow denotes the movable range of one observer to which the stereoscopic picture is presented by the first display unit 6-1, and the wavy-line arrow denotes the movable range of the other observer to which the stereoscopic picture is presented by the second display unit 6-2. In the stereoscopic picture generation apparatus 1D according to the embodiment, the rotatable range of the first display unit 6-1 is a range of 180 deg that is clockwise from the angle direction of 270 deg to the angle direction of 90 deg. Further, the rotatable range of the second display unit 6-2 is a range of 180 deg that is similarly clockwise from the angle direction of 90 deg to the angle direction of 270 deg.

Here, in the above movable ranges, the angle directions in which the stereoscopic pictures can be properly presented are eight angle directions of 0 deg, 45 deg, 90 deg, 135 deg, 180 deg, 225 deg, 270 deg and 315 deg, which are the same as the respective angle directions of the orientations of the dividing lines in the pupil division unit 22'.

FIG. 20 is an explanatory diagram for an internal configuration of the left-right picture individual-generation unit 4D. Here, FIG. 20 shows the pupil division unit 22', the picture pickup element 3, the control unit 7C and the memory 9, additionally.

Compared to the left-right picture individual-generation unit 4, the left-right picture individual-generation unit 4D is different in that a selector 41' is provided instead of the selector 41, and in that a first left-side addition unit 42'-1L is provided instead of the first left-side addition unit 42-1L, a first right-side addition unit 42'-1R is provided instead of the first right-side addition unit 42-1R, a second left-side addition unit 42'-2L is provided instead of the second left-side addition unit 42-2L, and a second right-side addition unit 42'-2R is provided instead of the second right-side addition unit 42-2R.

Moreover, there are differences in that the third left-side addition unit 42-3L to the fourth right-side addition unit 42-4R, the development processing unit 43-3L to the development processing unit 43-4R, and the third rotation processing unit 44-3L to the fourth rotation processing unit 44-4R are omitted, in that a second rotation processing unit 44'-2L is provided instead of the second rotation processing unit 44-2L and a second rotation processing unit 44'-2R is provided instead of the second rotation processing unit 44-2R, and in that a first rotation processing unit 44'-1L and a first rotation processing unit 44'-1R are added.

The selector 41' is the same as the selector 41, except that the output terminals TL3 to TR4 are omitted.

The output terminal TL1 of the selector 41' is connected with the first left-side addition unit 42'-1L, the output terminal TR1 is connected with the first right-side addition unit 42'-1R, the output terminal TL2 is connected with the second left-side addition unit 42'-2L, and the output terminal TR2 is connected with the second right-side addition unit 42'-2R.

Each addition unit 42' outputs the pickup picture after the addition, at the timing of response to an instruction from the control unit 7C.

Each rotation processing unit 44' rotates the input pickup picture by a rotation angle of an instruction by the control unit 7C.

Here, to the control unit 7C, the information indicating the angle directions of the positions of the observers is input by a signal Sa1 and a signal Sa2. These signals Sa1 and Sa2 may be signals that are obtained by the operation input of the observer through the operation unit, which is omitted in the figure, or may be signals that are obtained by the detection with a detection unit, which is provided to detect the rotation angles of the first display unit 6-1 and the second display unit 6-2.

Based on the information of the angle directions at the positions of the observers that is input by the respective signals Sa1 and Sa2, the control unit 7C instructs the first rotation processing unit 44'-1L to the second rotation processing unit 44'-2R on the rotation angle of the picture. In the embodiment, also, the placement angle of the picture pickup element 3 in the direction around the optical axis Ox is set such that the position where the angle direction is 0 deg is the reference position for observation. Therefore, the control unit 7C instructs the first rotation processing unit 44'-1L and the first rotation processing unit 44'-1R on a rotation angle that is the same angle deg as the angle deg of the angle direction given by the signal Sa1, and instructs the second rotation processing unit 44'-2L and the second rotation processing unit 44'-2R on a rotation angle that is the same angle deg as the angle deg of the angle direction given by the signal Sa2.

Thereby, it is possible to match the orientation of the subject X exhibited in the stereoscopic picture, with the orientation of the subject X when the subject X is actually observed.

Further, based on the information of the angle directions at the positions of the observers that is input by the respective signals Sa1 and Sa2 and the storage information of the control table 9a stored in the memory 9, the control unit 7C performs the shutter control of the pupil division unit 22', the control of the pickup timing of the picture pickup element 3, the selection control of the output terminals T of the selector 41', and the control of the picture output timing of the first left-side addition unit 42-1L to the second right-side addition unit 42-2R.

Hereinafter, these controls will be explained.

First, as an assumption, it is possible that for obtaining the left-eye pictures GL and right-eye pictures GR corresponding to the angle directions of the positions of the observers, similarly to the case of the first embodiment, the pickup pictures for the images that have passed through the individual areas A that constitute the pupil division unit 22' are acquired individually on the time axis, and then the acquired pickup pictures are added for each of the left-eye areas and right-eye areas corresponding to the angle directions of the positions of the observers.

However, in the case where, as the embodiment, the movement of the observers is allowable and the stereoscopic pictures have to be able to be presented in relatively many angle directions, the above individual acquisition of the pickup pictures for each area A, which increases the number of picture pickups by the picture pickup element 3, is undesirable.

Hence, the fifth embodiment achieves a reduction in the number of picture pickups by allowing light to simultaneously pass through the plurality of areas A.

FIG. 21 is an explanatory diagram for combinations of the areas A through which light can simultaneously pass. FIG. 21A, FIG. 21B and FIG. 21C exemplify the cases where the combination between the angle direction of the position of the one observer and the angle direction of the position of the other observer is "0 deg, 135 deg", "315 deg, 225 deg" and "0 deg, 180 deg", respectively.

In the case of FIG. 21A, since the left-eye area and right-eye area for the one observer at the position of 0 deg are split by the 0 deg-180 deg axis, the left-eye area is the areas A1 to A4 and the right-eye area is the areas A5 to A8. Further, since the left-eye area and right-eye area for the other observer at the position of 135 deg are split by the 135 deg-315 deg axis, the left-eye area is the areas A4 to A7 and the right-eye area is the areas A8 to A3.

From this, it is found that an overlapped part (A1 to A3) appears between the left-eye area (A1 to A4) for the one observer and the right-eye area (A8 to A3) for the other observer. Further, an overlapped part (A5 to A7) appears between the right-eye area (A5 to A8) for the one observer and the left-eye area (A4 to A7) for the other observer.

Here, in order to properly obtain the left-eye picture GL for an observer at the position in a certain angle direction, it is necessary that the picture pickup element 3 does not simultaneously pick up the images that have passed through the areas A constituting the left-eye area for the observer and the images that have passed through the areas A constituting the right-eye area for the observer (for preventing the crosstalk between the left-eye side and the right-eye side). Similarly, in order to properly obtain the right-eye picture GR for an observer at the position in a certain angle direction, it is necessary that the picture pickup element 3 does not simultaneously pick up the images that have passed through the areas A constituting the right-eye area for the observer and the images that have passed through the areas A constituting the left-eye area for the observer.

The left-eye areas and right-eye areas of the above overlapped parts fall within the left-eye areas and right-eye areas for the observers, respectively. Therefore, as for the areas A constituting the overlapped parts, the light can simultaneously pass, when properly obtaining the left-eye picture GL and right-eye picture GR for each observer.

Thus, as for the areas A corresponding to the overlapped parts between the one-eye areas for the observers, the light can simultaneously pass. That is, in the area A corresponding to the overlapped parts, the electronic shutters can be simultaneously opened.

In the case of FIG. 21A, the single-display period is divided into four periods t1 to t4, then, for example, in the period t1, only the first electronic shutter 22'a, second electronic shutter 22'b and third electronic shutter 22'c formed on the areas A1, A2 and A3 are opened, and in the period t2, only the fourth electronic shutter 22'd formed on the area A4 is opened. Further, in the period t3, only the fifth electronic shutter 22'e, sixth electronic shutter 22'f and seventh electronic shutter 22'g formed on the areas A5, A6 and A7 are opened, and in the period t4, only the eighth electronic shutter 22'h formed on the area A8 is opened.

Then, for the pickup picture signals obtained in the periods t1 to t4 respectively, the following selection control of the output terminals T of the selector 41' is performed, and thereby, the left-eye picture GL and the right-eye picture GR can be properly generated for each observer.

t1 . . . TL1 and TR2
t2 . . . TL1 and TL2
t3 . . . TR1 and TL2
t4 . . . TR1 and TR2

Meanwhile, in the case of FIG. 21B, there are four overlapped parts: the areas A1 and A8, the areas A2 and A3, the areas A4 and A5, and the areas A6 and A7.

In this case, the single-display period is divided into the periods t1 to t4, then, for example, in the period t1, only the first electronic shutter 22'*a* and eighth electronic shutter 22'*h* formed on the areas A1 and A8 are opened. In the period t2, only the second electronic shutter 22'*b* and third electronic shutter 22'*c* formed on the areas A2 and A3 are opened. In the period t3, only the fourth electronic shutter 22'*d* and fifth electronic shutter 22'*e* formed on the areas A4 and A5 are opened. In the period t4, only the sixth electronic shutter 22'*f* and seventh electronic shutter 22'*g* formed on the areas A6 and A7 are opened. Then, in this case, for the pickup picture signals obtained in the periods t1 to t4 respectively, the following selection control of the output terminals T of the selector 41' is performed, and thereby, the left-eye picture GL and the right-eye picture GR can be properly generated for each observer.

t1 . . . TL1 and TL2
t2 . . . TL1 and TR2
t3 . . . TR1 and TR2
t4 . . . TR1 and TL2

Further, in the case of FIG. 21C, there are two overlapped parts: the areas A1 to A4 and the areas A5 to A8. In this case, the division number of the single-display period is only two: the period t1 and the period t2. For example, in the period t1, only the first electronic shutter 22'*a* to the fourth electronic shutter 22'*d* formed on the areas A1 to A4 are opened, and in the period t2, only the fifth electronic shutter 22'*e* to the eighth electronic shutter 22'*h* formed on the areas A5 to A8 are opened.

Then, in this case, for the pickup picture signals obtained in the periods t1 and t2 respectively, the following selection control of the output terminals T of the selector 41' is performed, and thereby, the left-eye picture GL and the right-eye picture GR can be properly generated for each observer.

t1 . . . TL1 and TR2
t2 . . . TR1 and TL2

Here, the case where the division number of the single-display period is only "2" as FIG. 21C is the case where the angle difference between the angle directions at the positions of the respective observers is 180 deg. In other words, the division number of the single-display period is "4", in the other cases.

The explanation returns to FIG. 20.

In the control table 9*a*, the following information is stored for each combination of the angle directions of the positions of the observers.

a) The number of the periods t constituting the single-display period b) The correspondence relation between the period t and the area A to be opened c) The correspondence relation between the period t and the output terminal T to be selected in the selector 41'

The information of these a) to c) is determined such that the operation to allow the light to simultaneously pass through the overlapped parts between the one-eye areas for the observers as explained in FIG. 21 is actualized.

The control unit 7C performs the shutter control of the pupil division unit 22', the control of the pickup timing of the picture pickup element 3, the selection control of the output terminals T of the selector 41', and the control of the picture output timing of the first left-side addition unit 42-1L to the second right-side addition unit 42-2R, based on the information of the above a) to c) stored in the control table 9*a*.

The control of the pickup timing of the picture pickup element 3 and the control of the picture output timing of the first left-side addition unit 42-1L to the second right-side addition unit 42-2R are performed based on the information of the above a).

Thereby, it is possible to decrease the number of picture pickups by the picture pickup element 3 by allowing the light to simultaneously pass through the plurality of areas A, and to properly obtain the left-eye picture GL and right-eye picture GR for each observer.

5-2. Summary of Fifth Embodiment

As described above, in the stereoscopic picture generation apparatus 1D according to the fifth embodiment, the pupil division unit 22' has the areas A the number of which is a multiple of two and four or more. Further, the stereoscopic picture generation apparatus 1D includes the control unit 7C that, based on the information about the angle directions of the respective positions of the plurality of observers, performs such a control that incident light simultaneously passes through the plurality of areas A, which are of the areas A in the pupil division unit 22' and correspond to the overlapped parts between the one-eye areas for the observers.

This decreases the number of picture pickups by the picture pickup element 3 necessary for presenting a single piece of stereoscopic picture.

Therefore, it is possible to slow the shutter speed of the picture pickup element 3, resulting in an advantage when picking up a picture for a dark photographic subject or a fast-moving photographic subject.

Here, in the case where the division number of the areas A is "8" as the embodiment, if the number of the observers (the display units 6) is "6" or less, an overlapped area between one-eye areas for the observers can appear.

Alternatively, in the case where the division number of the areas A is "4" as the first embodiment, if the number of the observers is "2" or less, an overlapped area between one-eye areas for the observers can appear.

Therefore, the control according to the fifth embodiment can be performed, if the number of the display units 6 is "6" or less in the case where the division number of the areas A is "8", or if the number of the display units 6 is "2" or less in the case where the division number of the areas A is "4".

Further, the case of using the pupil division unit 22' that can allow light to pass through the areas A/block light for each of areas A as the first embodiment has been exemplified above, but, also, in the case of adopting a configuration in which the area A through which the light passes is selected by the illumination unit 8A and the pupil division unit 22A as the second embodiment, the control according to the fifth embodiment can be performed.

In this case, the information of the correspondence relation between the period t and the LD 82 to emit light is stored in the control table 9*a*, instead of the information of the above described b) (the information of the correspondence relation between the period t and the area A to be opened).

6. Sixth Embodiment

6-1. Configuration and Operation

FIG. 22 is a block diagram showing an internal configuration of a stereoscopic picture generation apparatus 1E according to a sixth embodiment.

The sixth embodiment relates to the adjustment of a parallax.

Compared to the stereoscopic picture generation apparatus 1 according to the first embodiment, the stereoscopic picture generation apparatus 1E is different in that an optical unit 2C is provided instead of the optical unit 2, and a control unit 7D is provided instead of the control unit 7. Compared to the optical unit 2, the optical unit 2C is different in that a pupil division unit 22C is provided instead of the pupil division unit 22.

FIG. 23 is an explanatory diagram for a configuration of the pupil division unit 22C.

In the pupil division unit 22C, the area A is further divided in the radial direction. Concretely, in the pupil division unit 22C according to the embodiment, each of the areas A1, A2, A3 and A4 in the pupil division unit 22 is divided into two in the radial direction. In the area A1, the inner area nearer to the optical axis Ox is referred to as the "area A1i", and the outer area is referred to as the "area A1o". The inner area in the area A2 is referred to as the "area A2i", and the outer area is referred to as the "area A2o". The inner area in the area A3 is referred to as the "area A3i", and the outer area is referred to as the "area A3o". The inner area in the area A4 is referred to as the "area A4i", and the outer area is referred to as the "area A4o".

In the pupil division unit 22C, an electronic shutter is formed in each of these areas A. The electronic shutters formed on the area A1i and area A1o are referred to as the "first inner electronic shutter 22Cai" and "first outer electronic shutter 22Cao", respectively. The electronic shutters formed on the area A2i and area A2o are referred to as the "second inner electronic shutter 22Cbi" and "second outer electronic shutter 22Cbo", respectively. The electronic shutters formed on the area A3i and area A3o are referred to as the "third inner electronic shutter 22Cci" and "third outer electronic shutter 22Cco", respectively. The electronic shutters formed on the area A4i and area A4o are referred to as the "fourth inner electronic shutter 22Cdi" and "fourth outer electronic shutter 22Cdo", respectively.

In FIG. 22, to the control unit 7D, an instruction of a parallax is performed by a signal Ss. In this case, the instruction of the parallax is performed by an operation input of the observer, and the signal Ss is an operation input signal from an operation unit, which is omitted in the figure. In the case of the embodiment, the instruction of the parallax is performed by two levels of "large" and "small". Here, in the embodiment, the effect by the parallax adjustment is provided to the respective observers (the respective display units 6) in common.

In response to an instruction of the "large" as the parallax, the control unit 7D performs such a control that the first outer electronic shutter 22Cao, second outer electronic shutter 22Cbo, third outer electronic shutter 22Cco and fourth outer electronic shutter 22Cdo formed on the areas A1o, A2o, A3o and A4o that are the outer areas of the areas A are closed sequentially and alternately.

On the other hand, in the case of an instruction of the "small" as the parallax, it executes such a control that the first inner electronic shutter 22Cai, second inner electronic shutter 22Cbi, third inner electronic shutter 22Cci and fourth inner electronic shutter 22Cdi formed on the areas A1i, A2i, A3i and A4i that are the inner areas of the areas A are closed sequentially and alternately.

In FIG. 23, for example, when focusing attention on an observer at the position of 0 deg, in the case where the control responding to the instruction of the "large" parallax is performed in the above described way, the images that have passed through the area A1o and area A2o are used for generating the left-eye picture GL, and the images that have passed through the area A3o and area A4o are used for generating the right-eye picture GR. On this occasion, the viewpoint centroid on the left-eye side, which is within the area formed by the area A1o and the area A2o, is at a relatively outer position to the optical axis Ox. Further, the viewpoint centroid on the right-eye side, which is within the area formed by the area A3o and the area A4o, is at a relatively outer position to the optical axis Ox, similarly.

In contrast to this, in the case where the control responding to the instruction of the "small" parallax is performed, the images that have passed through the area A1i and area A2i are used for generating the left-eye picture GL, and the images that have passed through the area A3i and area A4i are used for generating the right-eye picture GR. In this case, the viewpoint centroid on the left-eye side, which is within the area formed by the area A1i and the area A2i, is at a relatively inner position to the optical axis Ox. Further, the viewpoint centroid on the right-eye side, which is within the area formed by the area A3i and the area A4i, is at a relatively inner position to the optical axis Ox, similarly.

As understood in this regard, since the control responding to the instruction of the "large" or "small" parallax is performed in the above described way, it is possible to adjust the interval between the viewpoint centroid on the left-eye side and the viewpoint centroid on the right-eye side for each observer, to the "large" or the "small". Therefore, it is possible to adjust the parallax to the "large" or the "small".

Here, the example in which, by selecting only the outer areas or only the inner areas in the pupil division unit 22C, the parallax is adjusted by the two levels has been described above. However, for example, by adding a selection of the outer areas and the inner areas, other than the selection of only the outer areas or only the inner areas, the parallax can be adjusted by three levels. When selecting the outer areas and the inner areas, the viewpoint centroids on the left-eye side and the right-eye side are at nearly middle positions between those when selecting only the outer areas and those when selecting only the inner areas. Therefore, when the parallax by the selection of only the outer areas is the "large" and the parallax by the selection of only the inner areas is the "small", a parallax of "middle" can be actualized by the selection of the outer areas and the inner areas, allowing for a three-level adjustment.

Further, the example in which the adjustment of the parallax makes the effect on the respective observers in common has been described above, but it is possible that the adjustment of the parallax is individually performed for each observer.

Here, a modification of the parallax adjustment will be explained with reference to FIG. 24.

In this modification, as shown in FIG. 24A, a pupil division unit 22C' whose area is divided in a reticular pattern is used. In the case, the area is divided by three dividing lines parallel to the 0 deg-180 deg axis and three dividing lines parallel to the 90 deg-270 deg axis, and "16" areas are formed by the division. Of these dividing lines parallel to the 0 deg-180 deg axis and dividing lines parallel to the 90 deg-270 deg axis, the lines at the respective center positions intersect with the optical axis Ox.

In the pupil division unit 22C', lines configured by the plurality of areas that are arrayed in the direction parallel to the 0 deg-180 deg axis are referred to as "vertical lines V", and lines configured by the plurality of areas that are arrayed in the direction parallel to the 90 deg-270 deg axis are referred to as "horizontal lines H". As shown in FIG. 24B, the vertical lines V are referred to as a "vertical line V1o", a "vertical line V1i", a "vertical line V2i" and a "vertical line V2o", in the order from the angle direction of 90 deg to the angle direction of 270 deg. As shown in FIG. 24C, the horizontal lines H are referred to as a "horizontal line H1o", a "horizontal line H1i", a "horizontal line H2i" and a "horizontal line H2o", in the order from the angle direction of 0 deg to the angle direction of 180 deg.

In the embodiment, also, it is assumed that the angle directions of the positions of the observers are fixed to 0 deg, 90 deg, 180 deg and 270 deg.

In the embodiment, the electronic shutters formed on the respective areas in the pupil division unit 22'C are controlled in response to the instruction of the "large" or "small" parallax, as follows.

In the case of the "large" parallax
Period t1 . . . only V1o is opened
Period t2 . . . only H2o is opened
Period t3 . . . only V2o is opened
Period t4 . . . only H1o is opened
In the case of the "small" parallax
Period t1 . . . only V1i is opened
Period t2 . . . only H2i is opened
Period t3 . . . only V2i is opened
Period t4 . . . only H1i is opened Further, regardless of the "large" or "small" of the parallax, the selection control of the output terminals T of the selector 41 is performed as follows.
Period t1 . . . TL1 and TR3
Period t2 . . . TL2 and TR4
Period t3 . . . TR1 and TL3
Period t4 . . . TR2 and TL4

Here, in the modification, the addition units 42 are unnecessary.

In the above modification, also, it is possible to properly generate the left-eye picture GL and the right-eye picture GR for each of the observers at the positions of 0 deg, 90 deg, 180 deg and 270 deg, and to perform the adjustment of the parallax.

6-2. Summary of Sixth Embodiment

As described above, in the stereoscopic picture generation apparatus 1E according to the sixth embodiment, the areas A in the pupil division unit 22C are further divided in the radial direction of the pupil division unit 22C, and a picture selective-acquisition unit (the picture pickup element 3 and the control unit 7) selects one or a plurality of areas A from the areas A arrayed in the radial direction in the pupil division unit 22C, and acquires the pickup picture for the image that have passed through the selected area A.

Thereby, the pickup pictures that are different in the positions of the viewpoint centroids are selectively obtained. Therefore, it is possible to perform the adjustment of the parallax.

The parallax adjustment according to the sixth embodiment can be applied to the second to fifth embodiments, also.

7. Modification

The present technology is not limited to the concrete examples described above, and various modifications are possible.

For example, although the case where the division number of the areas A in the pupil division unit is a multiple of two and four or more has been exemplified, in the present technology, the division number of the areas A only has to be at least three or more. FIG. 25A exemplifies the case where three areas A (referred to as A1 to A3) are formed by division in the direction around the optical axis Ox. In this case, the areas A1 to A3 are arranged at intervals of 120 deg. From the positional relation of the areas A1 to A3 shown in the figure, it is found that the areas A1 and A3 correspond to the left-eye area and right-eye area of the observer at the position in the angle direction of 0 deg respectively, the areas A1 and A2 correspond to the right-eye area and left-eye area of the observer at the position in the angle direction of 120 deg respectively, and the areas A2 and A3 correspond to the right-eye area and left-eye area of the observer at the position in the angle direction of 240 deg respectively. In this regard, it is found that, by using the pupil division unit in which the three areas A are formed by division in the direction around the optical axis Ox, the left-eye picture GL and the right-eye picture GR can be properly generated for each of the three angle directions.

FIG. 25B exemplifies the case where five areas A (referred to as A1 to A5) are formed by division in the direction around the optical axis Ox. In this case, the areas A1 to A5 are arranged at intervals of 72 deg. Thereby, it is found that the left-eye picture GL and the right-eye picture GR can be properly generated for each of the angle directions of 0 deg, 72 deg, 144 deg, 216 deg and 288 deg. That is, in the case where the pupil division unit in which the five areas A are formed by division in the direction around the optical axis Ox is used, the left-eye picture GL and the right-eye picture GR can be properly generated for each of the five angle directions.

Thus, for properly presenting the respective stereoscopic pictures when the subject is observed from different angle directions, the division number of the areas in the pupil division unit only has to be three or more, and does not have to be a multiple of two.

In the second embodiment, as for the illumination unit 8A, the configuration in which the selective emission of the plurality of LDs to emit the lights with the different wavelengths respectively is performed has been exemplified, but it is possible to be a configuration using a light source that can change the emission wavelength by the control of the drive current, for example, a variable wavelength LD. Further, as the light source of the illumination unit 8A, another light-emitting element such as an LED (light emitting diode) can be used.

Further, in the case where, as the fifth embodiment, the information about the angle directions of the positions of the observers has to be acquired, the acquisition of the information about the angle directions may be performed by the automatic detection using cameras, for example.

Further, although the case where the present technology is applied to an operation microscope has been exemplified above, the present technology can be suitably applied also to another optical product, for example, an endoscope.

The effects described in the specification are just examples and are not limiting, and other effects are allowable.

Further, the present technology may be configured as described below.

(1)

An information processing apparatus, comprising: an image pickup element configured to acquire at least three images of an object, wherein each of the images respectively correspond to a different perspective of the object; and a control unit configured to selectively combine subsets of the images to generate a plurality of stereoscopic images.

(2)

The information processing apparatus according to (1), wherein the control unit is further configured to control the image pickup element to acquire the at least three images individually in sequential time periods.

(3)

The information processing apparatus according to (1) or (2), further comprising: a pupil having at least three shutter regions and configured to pass light to the image pickup element, wherein the control unit is further configured to selectively shutter subsets of the shutter regions to selectively block light.

(4)

The information processing apparatus according to (3), wherein the at least three shutter regions are rotationally symmetric.

(5)

The information processing apparatus according to (3) or (4), wherein the at least three shutter regions comprise at least three inner shutter regions and at least three outer shutter regions, the at least three inner shutter regions are rotationally symmetric, and the at least three outer shutter regions are rotationally symmetric.

(6)

The information processing apparatus according to any one of (1) to (5), further comprising: a selector configured to determine which of the at least three images correspond to a left-side and a right-side, respectively; and an addition unit configured to add the images corresponding to a left-side to generate a left-eye image and the images corresponding to a right-side to generate a right-eye image, wherein the control unit is further configured to combine the left-eye image and the right-eye image to generate a respective stereoscopic image.

(7)

The information processing apparatus according to any one of (1) to (6), wherein the plurality of stereoscopic images is at least three stereoscopic images.

(8)

The information processing apparatus according to any one of (1) to (7), wherein the respective ones of the plurality of stereoscopic images stereoscopic image include a left-eye image and a right-eye image.

(9)

The information processing apparatus according to any one of (1) to (8), wherein the at least three images are images obtained by a surgical microscope or an endoscope.

(10)

A non-transitory computer readable medium containing instructions which, when executed, cause a processor to perform operations comprising: accessing at least three images of an object, wherein each of the images correspond to a different perspective of the object; and selectively combining subsets of the images to generate a plurality stereoscopic images.

(11)

The non-transitory computer readable medium according to (10), wherein the operation of accessing comprises controlling, by a control unit, an image pickup element to acquire the at least three images individually in sequential time periods.

(12)

The non-transitory computer readable medium according to (10) or (11), wherein the operation of accessing comprises: passing light through a pupil to an image pickup element, the pupil having at least three shutter regions; selectively shuttering, by a control unit, subsets of the shutter regions to selectively block light.

(13)

The non-transitory computer readable medium according to (12), wherein the at least three shutter regions are rotationally symmetric.

(14)

The non-transitory computer readable medium according to (12) or (13), wherein the at least three shutter regions comprise at least three inner shutter regions and at least three outer shutter regions, the at least three inner shutter regions are rotationally symmetric, and the at least three outer shutter regions are rotationally symmetric.

(15)

The non-transitory computer readable medium according to any one of (10) to (14), wherein the operation of combining comprises: determining which of the at least three images correspond to a left-side and a right-side, respectively; adding the images corresponding to a left-side to generate a left-eye image and the images corresponding to a right-side to generate a right-eye image; and combining the left-eye image and the right-eye image to generate a stereoscopic image.

(16)

The non-transitory computer readable medium according to any one of (10) to (15), wherein the plurality of stereoscopic images is at least three stereoscopic images.

(17)

The non-transitory computer readable medium according to any one of (10) to (16), wherein the respective ones of the plurality of stereoscopic images stereoscopic image include a left-eye image and a right-eye image.

(18)

The non-transitory computer readable medium according to any one of (10) to (17), wherein the at least three images are images obtained by a surgical microscope or an endoscope.

(19)

An electronic system, comprising: an optical unit; the stereoscopic image generation device; and a plurality of display units, wherein the stereoscopic image generation device includes an information apparatus comprising: an image pickup element configured to acquire at least three images of an object, wherein each of the images respectively correspond to a different perspective of the object; and a control unit configured to selectively combine subsets of the images to generate a plurality of stereoscopic images.

(20)

A method of processing information, comprising: accessing at least three images of an object, wherein each of the images correspond to a different perspective of the object; and selectively combining subsets of the images to generate a plurality stereoscopic images.

Additionally, the present technology may also be configured as below.

(1)

A stereoscopic picture generation apparatus including:

a pupil division unit that light through a condensing lens enters, the pupil division unit having three or more areas, the condensing lens condensing light from a photographic subject, the three or more areas being formed by division in a direction around an optical axis; and a picture selective-acquisition unit that includes a picture pickup element configured to form pictures for images that have passed through the pupil division unit, the picture selective-acquisition unit selectively acquiring pickup pictures for the respective images that have passed through the different areas in the pupil division unit, by time division or by utilizing at least difference in wavelength of the respective images.

(2)

The stereoscopic picture generation apparatus according to (1), wherein the pupil division unit has the areas a number of which is a multiple of two and four or more, and the stereoscopic picture generation apparatus further includes:

a picture addition unit that adds a plurality of the pickup pictures acquired by the picture selective-acquisition unit in different combination.

(3)

The stereoscopic picture generation apparatus according to (1) or (2), wherein the picture selective-acquisition unit acquires, by time division, the pickup pictures for the respective images that have passed through the different areas in the pupil division unit, with the picture pickup element.

(4)

The stereoscopic picture generation apparatus according to (3), wherein the pupil division unit has the areas a number of which is a multiple of two and four or more, and the stereoscopic picture generation apparatus further includes:

a control unit that, based on information about angle directions of positions of a plurality of observers, performs a control in a manner that incident light simultaneously passes through a plurality of the areas out of the areas in the pupil division unit, the plurality of areas corresponding to an overlapped part between one-eye areas for the observers.

(5)

The stereoscopic picture generation apparatus according to (3) or (4), wherein the pupil division unit is configured to be capable of allowing incident light to pass through the areas/blocking incident light for each of the areas, and the picture selective-acquisition unit sequentially selects the area through which the incident light is to pass, and sequentially receives an image that has passed through the selected area with the picture pickup element.

(6)

The stereoscopic picture generation apparatus according to (3) or (4), wherein the pupil division unit is configured in a manner that lights with different wavelength bands selectively pass through the respective areas, the lights having the respective wavelength bands of a red-color wavelength band, a green-color wavelength band and a blue-color wavelength band, the picture pickup element is configured to be capable of receiving the lights with the red-color wavelength band, the green-color wavelength band and the blue-color wavelength band, and the picture selective-acquisition unit includes a variable wavelength illumination unit configured to be capable of selectively emitting, as illumination light to the photographic subject, lights with the same wavelength bands as the lights with the wavelength bands that pass through the individual areas in the pupil division unit, the picture selective-acquisition unit sequentially emitting the lights with the different wavelength bands with the variable wavelength illumination unit, and sequentially receiving the lights that have passed through the pupil division unit, for each switching of emission wavelengths of the variable wavelength illumination unit with the picture pickup element.

(7)

The stereoscopic picture generation apparatus according to (1) or (2), wherein the pupil division unit is configured in a manner that lights with different wavelength bands selectively pass through the areas, and the picture pickup element arranges a plurality of wavelength filters at different positions on a picture pickup surface, the plurality of wavelength filters selectively transmitting lights with the same wavelength bands as the lights that have passed through the different areas in the pupil division unit.

(8)

The stereoscopic picture generation apparatus according to (7), wherein the pupil division unit is configured in a manner that lights with different wavelength bands selectively pass through the respective areas, the lights having the respective wavelength bands of a red-color wavelength band, a green-color wavelength band and a blue-color wavelength band, and the picture pickup element arranges the plurality of wavelength filters at the different positions on the picture pickup surface, the plurality of wavelength filters selectively transmitting lights with the same wavelength bands as the lights that have passed through the different areas in the pupil division unit.

(9)

The stereoscopic picture generation apparatus according to (1) or (2), wherein the picture selective-acquisition unit selectively acquires the pickup pictures for the respective images that have passed through the different areas, by utilizing difference in wavelength and polarization of the respective images.

(10)

The stereoscopic picture generation apparatus according to (9), wherein the pupil division unit includes a wavelength separation element on which a plurality of pupil-side wavelength filters are formed, and a polarization separation element on which a plurality of pupil-side polarizing plates are formed, the plurality of pupil-side wavelength filters selectively transmitting lights with different wavelength bands, the lights having the respective wavelength bands of a red-color wavelength band, a green-color wavelength band and a blue-color wavelength band, the plurality of pupil-side polarizing plates selectively transmitting different polarized lights, the pupil division unit being configured in a manner that the wavelength separation element and the polarization separation element are arranged so as to be overlapped in the optical axis direction and lights having different combinations of the wavelength bands and the polarizations for each of the areas selectively pass through the pupil division unit, and the picture pickup element includes a plurality of image-surface-side wavelength filters and a plurality of image-surface-side polarizing plates, the plurality of image-surface-side wavelength filters selectively transmitting lights with the same wavelength bands as the lights that have passed through the different pupil-side wavelength filters, the plurality of image-surface-side polarizing plates selectively transmitting polarized lights in the same polarization directions as the polarized lights that have passed through the different pupil-side polarizing plates, the image-surface-side wavelength filters and the image-surface-side polarizing plates being arranged in different combination at different positions on a surface parallel to a picture pickup surface so as to be overlapped in the optical axis direction.

(11)
The stereoscopic picture generation apparatus according to any of (1) to (10),
wherein the areas in the pupil division unit are further divided in a radial direction of the pupil division unit, and
the picture selective-acquisition unit selects one or a plurality of areas from the areas in the pupil division unit arrayed in the radial direction, and acquires a pickup picture for an image that has passed through the selected area.

(12)
The stereoscopic picture generation apparatus according to any of (1) to (11), further including:
a picture rotation processing unit that rotates a left-eye picture and a right-eye picture obtained based on the pickup picture acquired by the picture selective-acquisition unit.

It should be understood by those skilled in the art that various modifications, combinations, sub-combinations and alterations may occur depending on design requirements and other factors insofar as they are within the scope of the appended claims or the equivalents thereof.

REFERENCE SIGNS LIST 1, 1A to 1E stereoscopic picture generation apparatus
2, 2', 2A to 2C optical unit
22, 22', 22A to 22C, 22C' pupil division unit
22a to 2d, 22'a to 22'b, 22Ca to 22Cd electronic shutter
22Aa to 22Ad wavelength filter
3, 3A, 3B picture pickup element
3Ba, 3Bb polarizing plate
4, 4A to 4D left-right picture individual-generation unit
7, 7A to 7C control unit
24 wavelength separation element
25 polarization separation element

The invention claimed is:

1. An image sensor configured to acquire at least three images of an object, wherein each of the images respectively correspond to a different perspective of the object with respect to the object;
a pupil having at least three shutter regions, wherein each of the shutter regions corresponds to a different angular range of the object with respect to an optical axis of the pupil, and each of the shutter regions corresponds to one of the at least three images having the different perspective of the object with respect to the object;
a processor configured to selectively combine subsets of the images to generate a plurality of stereoscopic images for an observer at a plurality of angle directions to the object respectively, including
determining which of the at least three images correspond to a left-side of the object and a right-side of the object, respectively; and
joining the images determined to correspond to one of the left-side of the object and the right-side of the object to generate a first side-eye image corresponding to a certain angle direction selected from the plurality of angle directions, the first image and the second image being included in the images acquired by the image sensor, and the second image corresponding to a different perspective of the object than the first image.

2. The information processing apparatus according to claim 1, wherein the processor is further configured to control the image sensor to acquire the at least three images individually in sequential time periods.

3. The information processing apparatus according to claim 1, further comprising:
a pupil having at least three shutter regions and configured to pass light to the image sensor,
wherein the processor is further configured to selectively shutter subsets of the shutter regions to selectively block light.

4. The information processing apparatus according to claim 3, wherein the at least three shutter regions are rotationally symmetric.

5. The information processing apparatus according to claim 3, wherein
the at least three shutter regions comprise at least three inner shutter regions and at least three outer shutter regions,
the at least three inner shutter regions are rotationally symmetric, and
the at least three outer shutter regions are rotationally symmetric.

6. The information processing apparatus according to claim 1, wherein the processor is further configured to:
join images determined to correspond to the other of the left-side of the object and the right-side of the object to generate a second side-eye image,
combine the first side-eye image and the second side-eye image to generate a stereoscopic image.

7. The information processing apparatus according to claim 1, wherein the plurality of stereoscopic images is at least three stereoscopic images.

8. The information processing apparatus according to claim 1, wherein respective ones of the plurality of stereoscopic images include a left-eye image and a right-eye image.

9. The information processing apparatus according to claim 1, wherein the at least three images are images obtained by a surgical microscope or an endoscope.

10. A non-transitory computer readable medium storing instructions which, when executed, cause a processor to perform operations comprising:
accessing at least three images of an object, wherein each of the images correspond to a different perspective of the object with respect to the object;
passing light through a pupil having at least three shutter regions, wherein each of the shutter regions corresponds to a different angular range of the object with respect to an optical axis of the pupil, and each of the shutter regions corresponds to one of the at least three images having the different perspective of the object with respect to the object;
selectively combining subsets of the images to generate a plurality of stereoscopic images for an observer at a plurality of angle directions to the object respectively, including determining which of the at least three images correspond to a left-side of the object and a right-side of the object, respectively; and
joining a first image and a second image determined to correspond to one of the left-side of the object and the right-side of the object to generate a first side-eye image corresponding to a certain angle direction selected from the plurality of angle directions, the first image and the second image being included in the images acquired by the image sensor, and the second image corresponding to a different perspective of the object than the first image.

11. The non-transitory computer readable medium according to claim 10, wherein the accessing comprises controlling an image sensor to acquire the at least three images individually in sequential time periods.

12. The non-transitory computer readable medium according to claim 10, wherein the accessing comprises:
passing light through a pupil to an image sensor, the pupil having at least three shutter regions;
selectively shuttering subsets of the shutter regions to selectively block light.

13. The non-transitory computer readable medium according to claim 12, wherein the at least three shutter regions are rotationally symmetric.

14. The non-transitory computer readable medium according to claim 12, wherein
the at least three shutter regions comprise at least three inner shutter regions and at least three outer shutter regions,
the at least three inner shutter regions are rotationally symmetric, and
the at least three outer shutter regions are rotationally symmetric.

15. The non-transitory computer readable medium according to claim 10, wherein the combining comprises:
joining images determined to correspond to the other of the left-side of the object and the right-side of the object to generate a second side-eye image; and
combining the first side-eye image and the second-eye image to generate a stereoscopic image.

16. The non-transitory computer readable medium according to claim 10, wherein the plurality of stereoscopic images is at least three stereoscopic images.

17. The non-transitory computer readable medium according to claim 10, wherein respective ones of the plurality of stereoscopic images include a left-eye image and a right-eye image.

18. The non-transitory computer readable medium according to claim 10, wherein the at least three images are images obtained by a surgical microscope or an endoscope.

19. An electronic system, comprising:
an optical unit;
a stereoscopic image generation device; and
a plurality of display units, wherein the stereoscopic image generation device includes an information apparatus comprising:
an image sensor configured to acquire at least three images of an object, wherein each of the images respectively correspond to a different perspective of the object with respect to the object;
a pupil having at least three shutter regions, wherein each of the shutter regions corresponds to a different angular range of the object with respect to an optical axis of the pupil, and each of the shutter regions corresponds to one of the at least three images having the different perspective of the object with respect to the object;
a processor configured to selectively combine subsets of the images to generate a plurality of stereoscopic images for an observer at a plurality of angle directions to the object respectively, including
determining which of the at least three images correspond to a left-side of the object and a right-side of the object, respectively; and
joining a first image and a second image determined to correspond to one of the left side of the object and the right-side of the object to generate a first side-eye image corresponding to a certain angle direction selected from the plurality of angle directions, the first image and the second image being included in the images acquired by the image sensor, and the second image corresponding to a different perspective of the object than the first image.

20. A method of processing information, comprising:
accessing at least three images of an object, wherein each of the images correspond to a different perspective of the object with respect to the object;
passing light through a pupil having at least three shutter regions, wherein each of the shutter regions corresponds to a different angular range of the object with respect to an optical axis of the pupil, and each of the shutter regions corresponds to one of the at least three images having the different perspective of the object with respect to the object;
selectively combining subsets of the images to generate a plurality of stereoscopic images for an observer at a plurality of angle directions to the object respectively, including determining which of the at least three images correspond to a left-side of the object and a right-side of the object, respectively; and
joining a first image and a second image determined to correspond to one of the left side of the object and the right-side of the object, to generate a first side-eye image corresponding to a certain angle direction selected from the plurality of angle directions, the first, image and the second image being included in the images acquired by the image sensor, and the second image corresponding to a different perspective of the object than the first image.

* * * * *